United States Patent
Finn et al.

(10) Patent No.: US 11,250,956 B2
(45) Date of Patent: *Feb. 15, 2022

(54) DUPLICATION DETECTION IN CLINICAL DOCUMENTATION DURING DRAFTING

(71) Applicant: CERNER INNOVATION, INC., Kansas City, KS (US)

(72) Inventors: Christopher S. Finn, Liberty, MO (US); Margaret C. Kolm, Kansas City, MO (US); David J. O'Larte, Peculiar, MO (US); Steven S. Crooks, Gladstone, MO (US); Thomas C. Gifford, Kansas City, MO (US); J D Tyler, Leawood, KS (US)

(73) Assignee: CERNER INNOVATION, INC., Kansas City, KS (US)

(*) Notice: Subject to any disclaimer, the term of this patent is extended or adjusted under 35 U.S.C. 154(b) by 414 days.

This patent is subject to a terminal disclaimer.

(21) Appl. No.: 14/587,906

(22) Filed: Dec. 31, 2014

(65) Prior Publication Data

US 2016/0124613 A1 May 5, 2016

Related U.S. Application Data

(60) Provisional application No. 62/074,416, filed on Nov. 3, 2014.

(51) Int. Cl.
*G06F 3/048* (2013.01)
*G16H 70/00* (2018.01)
(Continued)

(52) U.S. Cl.
CPC .......... *G16H 70/00* (2018.01); *G06F 3/0484* (2013.01); *G06F 3/04842* (2013.01);
(Continued)

(58) Field of Classification Search
CPC .... G06F 19/32; G06F 19/3487; G06F 19/345; G06F 17/2785; G06F 19/3443;
(Continued)

(56) References Cited

U.S. PATENT DOCUMENTS

| | | | | |
|---|---|---|---|---|
| 5,713,350 A | * | 2/1998 | Yokota | G06Q 50/24 600/300 |
| 5,839,438 A | * | 11/1998 | Graettinger | A61B 5/00 600/300 |

(Continued)

OTHER PUBLICATIONS

Z. Huang, W. Dong, H. Duan and H. Li, "Similarity Measure Between Patient Traces for Clinical Pathway Analysis: Problem, Method, and Applications," in IEEE Journal of Biomedical and Health Informatics, vol. 18, No. 1, pp. 4-14, Jan. 2014, doi: 10.1109/JBHI.2013.2274281. (Year: 2014).*

(Continued)

*Primary Examiner* — Steven B Theriault
(74) *Attorney, Agent, or Firm* — Shook, Hardy and Bacon LLP

(57) ABSTRACT

Methods, systems, and computer-readable media are provided to detect similarities between two or more clinical documents. It is determined that a clinician is currently inputting data into a first clinical document that is associated with a patient. A selectable option is provided on a user interface into which the clinician is currently inputting the data. An indication is received that the selectable option has been selected by the clinician. An algorithm is applied to identify the second clinical document from a plurality of clinical documents. At least a portion of the inputted data in the first clinical document and at least a portion of data in the second clinical document are transformed to generate a new representation of the first clinical document that indicates (Continued)

the similarities that are potentially inaccurate or inappropriate between the first clinical document and the second clinical document.

19 Claims, 24 Drawing Sheets

(51) Int. Cl.
| | |
|---|---|
| G06F 3/04842 | (2022.01) |
| G06F 16/93 | (2019.01) |
| G06F 16/248 | (2019.01) |
| G06F 16/335 | (2019.01) |
| G06F 16/951 | (2019.01) |
| G06F 16/174 | (2019.01) |
| G06F 16/23 | (2019.01) |
| G06F 16/2458 | (2019.01) |
| G06F 16/2455 | (2019.01) |
| G06F 16/2457 | (2019.01) |
| G06F 3/0484 | (2022.01) |
| G16H 10/60 | (2018.01) |
| G16H 15/00 | (2018.01) |
| G06F 40/166 | (2020.01) |
| G06F 40/194 | (2020.01) |
| G06F 40/151 | (2020.01) |

(52) U.S. Cl.
CPC ...... *G06F 16/1748* (2019.01); *G06F 16/2358* (2019.01); *G06F 16/248* (2019.01); *G06F 16/2477* (2019.01); *G06F 16/24556* (2019.01); *G06F 16/24578* (2019.01); *G06F 16/335* (2019.01); *G06F 16/93* (2019.01); *G06F 16/951* (2019.01); *G06F 40/166* (2020.01); *G06F 40/194* (2020.01); *G16H 10/60* (2018.01); *G16H 15/00* (2018.01); *G06F 40/151* (2020.01)

(58) Field of Classification Search
CPC .............. G06F 17/27; G06F 17/30734; G06F 3/04842; G06F 17/2211; G06F 17/30011; G06F 17/30864; G06F 17/30554; G06F 17/30997; G06F 17/277; G06F 3/048; G06F 19/00; G06F 3/0484; G06F 1/203; G06F 17/24; G06F 17/30156; G06F 17/30253; G06F 17/30256; G06F 17/3053; G06F 17/30551; G06F 17/30684; G06F 17/30699; G06F 17/30867; G06F 19/326; G06F 3/0482; G06F 19/328; G06F 16/3344; G06F 17/218; G06F 17/2705; G06F 16/2455; G06F 16/951; G06F 17/241; G06F 16/24522; G06F 16/24578; G06F 16/2477; G06F 16/90328; G06F 16/93; G06F 16/3332; G06F 16/83; G06F 17/272; G06F 19/30; G06F 19/321; G06F 16/1748; G06F 16/24556; G06F 16/248; G06F 16/335; G06F 19/324; G06F 40/151; G06F 40/166; G06F 40/194; G06F 16/22; G06F 16/2365; G06F 16/2358; G06F 40/15; G16H 10/60; G16H 50/70; G16H 15/00; G16H 70/00; G06H 15/00
See application file for complete search history.

(56) References Cited

U.S. PATENT DOCUMENTS

| | | | | |
|---|---|---|---|---|
| 5,878,746 | A * | 3/1999 | Lemelson | G16H 70/60 600/407 |
| 5,941,944 | A * | 8/1999 | Messerly | G06F 16/10 709/203 |
| 6,286,000 | B1* | 9/2001 | Apte | G06F 17/30622 |
| 6,289,316 | B1* | 9/2001 | Aghili | G16H 70/20 705/3 |
| 6,915,254 | B1* | 7/2005 | Heinze | G06Q 10/10 704/9 |
| 7,254,587 | B2* | 8/2007 | Lee | G06F 17/30997 |
| 7,340,466 | B2* | 3/2008 | Odom | G06F 17/30616 |
| 7,447,643 | B1* | 11/2008 | Olson | G06F 19/3418 434/236 |
| 7,478,077 | B2* | 1/2009 | Berger | G06F 21/552 |
| 7,716,207 | B2* | 5/2010 | Odom | G06F 17/30616 707/705 |
| 7,860,844 | B2* | 12/2010 | Ebaugh | G06F 17/30613 707/696 |
| 7,899,825 | B2* | 3/2011 | Davis | G06F 17/30675 707/737 |
| 8,090,717 | B1* | 1/2012 | Bharat | G06F 17/30675 707/731 |
| 8,204,843 | B2* | 6/2012 | Bouchard | G06N 99/005 706/46 |
| 8,239,216 | B2* | 8/2012 | McCallie, Jr. | G06F 17/30657 705/2 |
| 8,280,844 | B2* | 10/2012 | Warn | G06F 21/55 707/607 |
| 8,285,734 | B2* | 10/2012 | Baras | G06F 17/30648 707/758 |
| 8,392,351 | B2* | 3/2013 | Brdiczka | G06Q 10/06 706/58 |
| 8,713,190 | B1* | 4/2014 | Goodall | H04L 41/0631 709/231 |
| 8,793,199 | B2* | 7/2014 | Syeda-Mahmood | G06F 19/3443 706/12 |
| 8,918,407 | B2* | 12/2014 | Doshi | G06Q 10/10 707/749 |
| 8,977,645 | B2* | 3/2015 | Crow | G06F 17/212 707/770 |
| 9,003,319 | B2* | 4/2015 | Linthicum | G06F 19/3406 715/771 |
| 9,058,543 | B2* | 6/2015 | Campbell | G06K 9/6202 |
| 9,165,039 | B2* | 10/2015 | Odom | G06F 17/30648 |
| 9,165,254 | B2* | 10/2015 | Duchon | G06Q 10/10 |
| 9,202,084 | B2* | 12/2015 | Moore | G06F 21/6245 |
| 9,280,536 | B2* | 3/2016 | Sayers | G06F 17/2765 |
| 9,350,552 | B2* | 5/2016 | Elmenhurst | G06K 9/3216 |
| 9,384,177 | B2* | 7/2016 | Sakurai | G06F 17/2288 |
| 9,465,828 | B2* | 10/2016 | Palmert | G06F 17/30979 |
| 9,514,103 | B2* | 12/2016 | Kletter | G06F 17/2211 |
| 9,652,670 | B1* | 5/2017 | Smyros | G06F 17/2785 |
| 9,921,731 | B2* | 3/2018 | Finn | G06F 3/04842 |
| 10,027,686 | B2* | 7/2018 | Zhao | H04L 43/04 |
| 10,127,229 | B2* | 11/2018 | Schijvenaars | G06F 16/93 |
| 10,127,289 | B2* | 11/2018 | Manning | G06F 16/24578 |
| 10,572,461 | B2* | 2/2020 | Bess | G06F 16/22 |
| 2003/0046114 | A1* | 3/2003 | Davies | G06Q 10/10 705/3 |
| 2003/0105638 | A1* | 6/2003 | Taira | G10L 15/005 704/275 |
| 2003/0154109 | A1* | 8/2003 | Martin | G06Q 50/24 705/3 |
| 2003/0208382 | A1* | 11/2003 | Westfall | G16H 10/65 705/3 |
| 2003/0216944 | A1* | 11/2003 | Stavis | G16H 70/60 705/3 |
| 2004/0078216 | A1* | 4/2004 | Toto | G16H 10/60 705/2 |
| 2004/0083452 | A1* | 4/2004 | Minor | G06F 19/24 717/109 |

(56) References Cited

U.S. PATENT DOCUMENTS

| | | | |
|---|---|---|---|
| 2004/0128267 A1* | 7/2004 | Berger | G06F 21/552 |
| 2004/0162834 A1* | 8/2004 | Aono | G06F 17/30675 |
| 2004/0167921 A1* | 8/2004 | Carson | G06F 17/30011 |
| 2004/0172294 A1* | 9/2004 | Dahlin | G16H 10/60 705/2 |
| 2005/0010863 A1* | 1/2005 | Zernik | G06F 17/2211 715/229 |
| 2005/0038311 A1* | 2/2005 | Kuth | G06F 19/325 600/1 |
| 2005/0060643 A1* | 3/2005 | Glass | G06F 17/241 715/205 |
| 2005/0108001 A1* | 5/2005 | Aarskog | G06F 17/271 704/10 |
| 2005/0165782 A1* | 7/2005 | Yamamoto | G06F 17/30017 |
| 2005/0289128 A1* | 12/2005 | Hamaguchi | G06F 16/313 |
| 2006/0015263 A1* | 1/2006 | Stupp | G06F 17/18 702/19 |
| 2006/0036619 A1* | 2/2006 | Fuerst | G06Q 10/10 |
| 2006/0112050 A1* | 5/2006 | Miikkulainen | G16H 10/60 706/46 |
| 2006/0173712 A1* | 8/2006 | Joubert | G16H 10/60 705/2 |
| 2006/0200253 A1* | 9/2006 | Hoffberg | G05B 15/02 700/19 |
| 2006/0259783 A1* | 11/2006 | Work | G16H 10/20 713/189 |
| 2007/0005396 A1* | 1/2007 | Lee | G16H 10/60 705/3 |
| 2007/0061171 A1 | 3/2007 | Ash et al. | |
| 2007/0129967 A1* | 6/2007 | Thompson | G06Q 10/06 705/2 |
| 2007/0143322 A1* | 6/2007 | Kothari | G06F 17/2211 |
| 2007/0299697 A1* | 12/2007 | Friedlander | G06F 19/322 705/3 |
| 2008/0016065 A1* | 1/2008 | Takaai | G06F 17/30011 |
| 2008/0208912 A1* | 8/2008 | Garibaldi | G06Q 10/06 |
| 2008/0247325 A1* | 10/2008 | Vaitaitis | H04L 43/0858 370/252 |
| 2008/0270120 A1* | 10/2008 | Pestian | G06F 17/2785 704/9 |
| 2009/0132276 A1* | 5/2009 | Petera | G06Q 50/22 705/2 |
| 2009/0281835 A1* | 11/2009 | Patwardhan | G16H 40/63 705/3 |
| 2010/0030780 A1* | 2/2010 | Eshghi | G06F 17/30271 707/758 |
| 2010/0104200 A1* | 4/2010 | Baras | G06F 19/324 382/209 |
| 2010/0131293 A1* | 5/2010 | Linthicum | G16H 10/60 705/3 |
| 2010/0131883 A1* | 5/2010 | Linthicum | G16H 40/63 715/771 |
| 2010/0179827 A1* | 7/2010 | McCallie, Jr. | G06F 16/3331 705/3 |
| 2011/0004626 A1* | 1/2011 | Naeymi-Rad | G06N 7/005 707/776 |
| 2011/0075901 A1* | 3/2011 | Nakamura | G16H 30/40 382/128 |
| 2011/0202370 A1* | 8/2011 | Green, III | G06Q 10/06 705/3 |
| 2011/0246234 A1 | 10/2011 | Irwin et al. | |
| 2011/0270843 A1* | 11/2011 | Albin | G06F 17/30864 707/741 |
| 2012/0060216 A1* | 3/2012 | Chaudhri | G06Q 50/22 726/21 |
| 2012/0066197 A1* | 3/2012 | Rana | G06F 19/322 707/706 |
| 2012/0078612 A1* | 3/2012 | Kandekar | G06F 17/2745 704/9 |
| 2012/0131507 A1* | 5/2012 | Sparandara | G16H 10/60 715/833 |
| 2012/0232930 A1* | 9/2012 | Schmidt | G06Q 10/10 705/3 |
| 2012/0278102 A1* | 11/2012 | Johnson | G06Q 10/10 705/3 |
| 2012/0283574 A1* | 11/2012 | Park | G06K 9/46 600/476 |
| 2012/0324350 A1* | 12/2012 | Rosenblum | G06F 40/205 715/256 |
| 2013/0035961 A1* | 2/2013 | Yegnanarayanan | G16Z 99/00 705/3 |
| 2013/0041685 A1* | 2/2013 | Yegnanarayanan | G16H 50/20 705/2 |
| 2013/0046558 A1* | 2/2013 | Landi | G06Q 50/24 705/3 |
| 2013/0080192 A1 | 3/2013 | Bucur et al. | |
| 2013/0085781 A1* | 4/2013 | Navani | G06Q 50/22 705/3 |
| 2013/0124523 A1* | 5/2013 | Rogers | G06F 19/32 707/737 |
| 2013/0182002 A1* | 7/2013 | Macciola | H04N 1/387 345/589 |
| 2013/0212090 A1* | 8/2013 | Sperling | G06F 16/3347 707/723 |
| 2013/0226616 A1* | 8/2013 | Nigam | G16H 70/60 705/3 |
| 2013/0246098 A1* | 9/2013 | Habboush | G06Q 10/087 705/3 |
| 2013/0297347 A1* | 11/2013 | Cardoza | G06F 16/36 705/3 |
| 2013/0297348 A1* | 11/2013 | Cardoza | G16H 40/20 705/3 |
| 2014/0029840 A1* | 1/2014 | Jebara | G06K 9/6256 382/159 |
| 2014/0136237 A1 | 5/2014 | Anderson et al. | |
| 2014/0149132 A1* | 5/2014 | DeHaan | G16H 10/60 705/2 |
| 2014/0181128 A1* | 6/2014 | Riskin | G06F 16/3344 707/756 |
| 2014/0200921 A1* | 7/2014 | Hamill | G16H 10/60 705/3 |
| 2014/0244300 A1* | 8/2014 | Bess | G06F 16/22 705/3 |
| 2014/0272832 A1* | 9/2014 | Mitkov | G09B 7/00 434/219 |
| 2014/0278448 A1* | 9/2014 | Sadeghi | G16H 15/00 705/2 |
| 2014/0280353 A1* | 9/2014 | Delaney | G06F 17/30734 707/794 |
| 2014/0297269 A1* | 10/2014 | Qian | G06F 17/2785 704/9 |
| 2014/0304003 A1* | 10/2014 | Sethumadhavan | G16H 40/20 705/3 |
| 2014/0343925 A1* | 11/2014 | Mankovich | G06F 16/36 704/9 |
| 2014/0350961 A1* | 11/2014 | Csurka | G06F 19/322 705/3 |
| 2014/0358010 A1* | 12/2014 | Battiwalla | A61B 5/4851 600/476 |
| 2014/0365232 A1* | 12/2014 | Sadeghi | G06F 19/345 705/2 |
| 2014/0365239 A1* | 12/2014 | Sadeghi | G06F 19/321 705/3 |
| 2015/0012887 A1* | 1/2015 | Ash | G06F 3/04817 715/835 |
| 2015/0052058 A1* | 2/2015 | McCown | G06Q 50/22 705/51 |
| 2015/0134594 A1* | 5/2015 | Sethumadhavan | G06F 40/169 707/602 |
| 2015/0227278 A1* | 8/2015 | Bruce | G16H 10/60 715/761 |
| 2015/0339442 A1* | 11/2015 | Oleynik | G06F 19/324 705/3 |
| 2015/0356646 A1* | 12/2015 | Spitznagel | G16H 40/20 705/2 |
| 2016/0048655 A1 | 2/2016 | Maitra et al. | |

(56) References Cited

U.S. PATENT DOCUMENTS

| | | | |
|---|---|---|---|
| 2016/0048780 A1* | 2/2016 | Sethumadhavan | G06Q 50/24 |
| | | | 705/2 |
| 2016/0071226 A1* | 3/2016 | Karale | G06Q 10/00 |
| | | | 705/3 |
| 2016/0098456 A1* | 4/2016 | Contreras | G06F 16/2455 |
| | | | 705/3 |
| 2016/0125169 A1 | 5/2016 | Finn et al. | |
| 2016/0147946 A1* | 5/2016 | Von Reden | G16H 10/60 |
| | | | 705/3 |
| 2016/0147948 A1 | 5/2016 | Hewett et al. | |
| 2016/0253350 A1* | 9/2016 | Moulik | G06F 16/2365 |
| | | | 707/694 |
| 2016/0283670 A1* | 9/2016 | Tubman | G16H 40/63 |
| 2016/0283680 A1* | 9/2016 | Deng | G16H 10/60 |
| 2016/0314278 A1* | 10/2016 | Mabotuwana | G16H 30/40 |
| 2017/0039326 A1 | 2/2017 | Stankiewicz et al. | |
| 2017/0116373 A1* | 4/2017 | Ginsburg | G16H 40/20 |
| 2018/0011974 A1* | 1/2018 | Schneider | G06F 16/5846 |
| 2018/0108433 A1* | 4/2018 | Mahoney | G16H 10/20 |
| 2020/0027560 A1* | 1/2020 | Ling | G16H 10/60 |

OTHER PUBLICATIONS

S. Dalmiani, A. Taddei, M. Glauber and M. Emdin, "An informative system for structured data management to build a cardiological multidimensional database," Computers in Cardiology, Memphis, TN, USA, 2002, pp. 369-372, doi: 10.1109/CIC.2002.1166786. (Year: 2002).*

I. Song and N. V. Marsh, "Anonymous Indexing of Health Conditions fora Similarity Measure," in IEEE Transactions on Information Technology in Biomedicine, vol. 16, No. 4, pp. 737-744, Jul. 2012, doi: 10.1109/TITB.2012.2194717. (Year: 2012).*

D. Wilson, D. O'Sullivan, E. McLoughlin and M. Bertolotto, "Case-Based Decision Support for Intelligent Patient Knowledge Management," 2006 3rd International IEEE Conference Intelligent Systems, London, 2006, pp. 130-135, doi: 10.1109/IS.2006.348406. (Year: 2006).*

Disclosed Anonymously, System and method for analysing data records utilizing a touch screen interface, The IP.com Journal, Jan. 24, 2011, pp. 1-33 (Year: 2011).*

Final Office Action dated Dec. 28, 2017 in U.S. Appl. No. 14/587,853, 6 pages.

Notice of Allowance dated Jan. 11, 2018 in U.S. Appl. No. 14/587,695, 9 pages.

Non-Final Office Action dated Jun. 2, 2017 in U.S. Appl. No. 14/587,853, 13 pages.

Non-Final Office Action dated Jul. 13, 2017 in U.S. Appl. No. 14/587,695, 11 pages.

Notice of Allowance dated Apr. 17, 2018 in U.S. Appl. No. 14/587,853, 9 pages.

* cited by examiner

| Capability | Previous note | Evaluated note |
|---|---|---|
| Text similarity<br><br>*Simple text comparison* | buPROPrion 150 mg daily, prednisone 60 mg daily, furosemide 40 | buPROPrion 150 mg daily, prednisone 80 mg daily, furosemide 40 |
| Features<br><br>*Significant similarities, in context of clinical note* | Diabetic, with Hx CHF. MI 2 mos ago. Admitted this a.m. from ED. | Diabetic, with Hx CHF. MI 2 mos ago. Admitted this a.m. from ED. |
| Document similarity "score"<br><br>*Rate entire document for overall similarity* | | Score:<br>High risk<br>Low risk<br>Appropriate |

*FIG. 3.*

Similarities Highlighted — 402

Progress Note 2014 May 11 17:43 — 404

Patient: Doe, Jane

Subjective
Pt "feels well" this a.m. Affect and appearance improved. Still c/o cough, unchanged from yesterday. Appetite is good; she finished her breakfast.

Review of Systems
All body systems were reviewed. ROS is negative except as indicated.

Medications
buPROPion XL 150 mg oral daily
prednisone 60 mg oral daily
furosemide 40 mg oral daily

Progress Note 2014 May 12 18:00 — 406

Patient: Doe, Jane

Subjective
Pt "feels well" this a.m. Affect and appearance improved. Still c/o cough, improved from yesterday. Appetite is good; she finished her breakfast.

Review of Systems
All body systems were reviewed. ROS is negative except as indicated.

Medications
buPROPion XL 150 mg oral daily
prednisone 80 mg oral daily
furosemide 40 mg oral daily

*FIG. 4.*

Differences Highlighted

Progress Note 2014 May 11 17:43

Patient: Doe, Jane

Subjective
Pt "feels well" this a.m. Affect and appearance improved. Still c/o cough, unchanged from yesterday. Appetite is good; she finished her breakfast.

Review of Systems
All body systems were reviewed. ROS is negative except as indicated.

Medications
buPROPrion XL 150 mg oral daily
prednisone 60 mg oral daily
furosemide 40 mg oral daily

Progress Note 2014 May 12 18:00

Patient: Doe, Jane

Subjective
Pt "feels well" this a.m. Affect and appearance improved. Still c/o cough, improved from yesterday. Appetite is good; she finished her breakfast.

Review of Systems
All body systems were reviewed. ROS is negative except as indicated.

Medications
buPROPrion XL 150 mg oral daily
prednisone 80 mg oral daily
furosemide 40 mg oral daily

*FIG. 5.*

| Grade | Document | Provider | Comparison to Previous Note |
|---|---|---|---|
| High risk | Progress Note 2014-May-12 9:00 | Alvarez | IH, PE, IP, PLAN unchanged. IH: "Post-Op day 3" PLAN: "Greater than 30 minutes spent removing surgical staples today." |
| High risk | Progress Note 2014-May-8 11:30 | Brown | IH, ROS, PE, IP, PLAN unchanged. ROS: "Intermittent nausea during the night last night; vomited twice." |
| Moderate risk | Progress Note 2014-May-9 17:30 | Cardiff | IH, ROS, PE unchanged IH: "ABX day 5" |
| Moderate risk | Progress Note 2014-May-10 19:15 | Denton | IH, ROS, PE, PLAN unchanged |
| Possible risk | Progress Note 2014-May-12 20:00 | Eng | IH, ROS, PE unchanged IH: "Reports no cramping today." |

JACKSON, ANDY

| REVIEW | ORDER | DOCUMENT | + | 1106 | | | |
|---|---|---|---|---|---|---|---|

DOCUMENTS 1108 | LAST 24 HOURS | CURRENT ENCOUNTER | YEAR ▶ | | | □□ | ≡ ▼

- VITALS
- PROBLEMS
- MEDICATIONS
- LABS
- DIAGNOSTICS
- PATHOLOGY
- MICROBIOLOGY
- HISTORIES
- INTAKE & OUTPUT
- SUBJECTIVE/HPI
- OBJECTIVE/PE
- NEW ORDER EN...
- COMPONENT
- COMPONENT
- COMPONENT

ALL NOTE TYPES (9) | CLINIC NOTE (5) — 1102 | DISCHARGE SUMMARY (2) | ONCOLOGY REPORT (2)

JUL Y 2, 2014 8:15 AM | JUN 23, 2014 10:03 AM | JULY 21, 2014 8:15 AM | JULY 22, 2014 2:00 PM | JULY 25, 2014 11:03 AM

ONCOLOGY REPORT RICHARDS MD, PAUL | ONCOLOGY REP... JEFFERSON MD, TOM [2] | CLINIC NOTE ALLEN MD, MAY | ONCOLOGY REPORT DAY MD, BOB | CLINIC NOTE SMITH MD, JOHN [1]

< PREVIOUS

LOREM IPSUM T... JEFFERSON MD, TOM | 6/23/14 ... [2] | MUSPI MER... WINTERS MD, DOUG | 7/25/14 11:03 AM | [1]
— 1104

SUBJECTIVE

VIVAMUS EU LACUS ET LEO TEMPUS EUISMOD A DIGNISSIM LECTUS. ALIQUA VESTIBULUM, LOREM QUIS VULPUTATE RHONCUS, ODIO MAGNA EGESTAS ENIM, ID SOLLICITUDIN SAPIEN LOREM VEL LIGULA. ALIQUAM AT LECTUS ANTE.

VESTIBULUM IACULIS TINCIDUNT MI, AT MALESUADA ARCU FERMENTUM VEL. PELLENTESQUE HABITANT MORBI TRISTIQUE SENECTUS ET.

CRAS VEHICULA SIT AMET SAPIEN VOLUTPAT FACILISIS. DONEC TRISTIQUE LIGULA URNA, ID PORTTITOR MAURIS CONSECTETUR QUIS. PRAESENT CONSECTETUR ELEIFEND AUGUE, AT ULTRICIES NISL PRETIUM SED.

SUBJECTIVE

NAM NON DICTUM URNA. FUSCE ULTRICES, LIGULA AT SUSCIPIT PORTA, NEQUE ODIO PLACERAT TORTOR, AT CONDIMENTUM ERAT TELLUS VITAE QUAM. INTEGER UT URNA ET LOREM LOBORTIS PORTTITOR.

PRAESENT MI AUGUE, MOLLIS LACINIA NEQUE A, DIGNISSIM SEMPER RISUS. PROIN VEL LIBERO NEC EX ELEMENTUM ULTRICES TINCIDUNT VEL NISI. PHASELLUS PLACERAT MAURIS QUIS TRISTIQUE MALESUADA.

DUIS VEHICULA, EST AT EFFICITUR CONSEQUAT, ERAT MAGNA VENENATIS ODIO.

REGAN, THEODORE
REGAN, THEODORE  GENDER: MALE  DOB: 4/10/1990  MRN: 00002092  ATTENDING: WASHINGTON MD, GEORGE
ALLERGIES: AMOXICILLIN  ISOLATION:  AGE: 24 YEARS  LOC:  DOSE WT:

MENU - INPATIENT

- WORKFLOW
- PATIENT SUMMARY
- CONTINUUM CARE...
- GOALS MANAGEMENT
- RESULTS REVIEW
- ORDERS
- MEDICATION LIST
- DOCUMENTATION
- ACTIVITIES
- ALLERGIES
- BODY SYSTEMS VIEW
- CHART SEARCH
- CLINICAL RESEARCH
- COMMUNITY VIEW
- DATA RECONCILIATION
- DIAGNOSIS & PROB.
- DISCHARGE SUMMARY
- GROWTH CHART
- HEALTH MAINTENANCE
- HISTORIES
- IMMUNIZATION SCHEDULE
- INTERACTIVE VIEW AND ...
- INTERDISCIPLINARY RO...

+ADD ▾ 📄

PROGRESS NOTE | LIST

CALIBRI ▾ | 14 ▾ | ... | B | I | U ...

1402  1406
  ⭐ 15         UNIQUENESS SCORE  1404

ADMISSION DAY

HISTORY OF PRESENT ILLNESS
MR. BAKER COMES IN TODAY EXPERIENCING SHORTNESS OF BREATH FOR THE LAST 2 DAYS.

REVIEW OF SYSTEMS
CONSTITUTIONAL: [NO FEVERS, CHILLS, SWEATS]
EYE: [NO RECENT VISUAL PROBLEMS]
ENMT: [NO EAR PAIN, NASAL CONGESTION, SORE THROAT]
RESPIRATORY: [NO SHORTNESS OF BREATH, COUGH]
CARDIOVASCULAR: [NO CHEST PAIN, PALPITATIONS, SYNCOPE]
GASTROINTESTINAL: [NO NAUSEA, VOMITING, DIARRHEA]
GENITOURINARY: [NO HEMATURIA]
HEMA/LYMPH: [NEGATIVE FOR BRUISING TENDENCY, SWOLLEN LYMPH GLANDS]
ENDOCRINE: [NEGATIVE FOR EXCESSIVE THIRST, EXCESSIVE HUNGER]
MUSCULOSKELETAL: [NO BACK PAIN, NECK PAIN, JOINT PAIN, MUSCLE PAIN, LESS RANGE OF MOTION]
INTEGUMENTARY: [NO RASH, PRURITUS, ABRASIONS]
NEUROLOGIC: [ALERT & ORIENTED X 4]
PSYCHIATRIC: [NO ANXIETY, DEPRESSION]

MEDICATIONS
  ATORVASTATIN 20 MG ORAL TABLET, 20 MG, 1 TABS, ORAL, DAILY

ALLERGIES
AMOXICILLIN

NOTE DETAILS: PROGRESS NOTE – GENERIC, GIF... | SIGN/SUBMIT | SAVE | SAVE & CLOSE | CANCEL

REGAN, THEODORE ☒

| REGAN, THEODORE | GENDER: MALE | DOB: 4/10/1990 | MRN: 00002092 | ATTENDING: WASHINGTON MD, GEORGE |
| ALLERGIES: AMOXICILLIN | ISOLATION: | AGE: 24 YEARS | LOC: | DOSE WT: |

≪ ≫ ▾ |⌂ DOCUMENTATION

+ADD ▾ 🔍 📋 | 📄

PROGRESS NOTE | LIST

CALIBRI ▾ | 14 ▾ | 🗲 📋 📋 ⤺ ⤻ | B  I  U ⎯ ▾ ☐▾ | ≣ ≣ ≣ ≣ | 🔖

PHYSICAL EXAM ☐☐☐
VITALS & MEASUREMENTS
NO QUALIFYING DATA AVAILABLE
GENERAL: [ALERT AND ORIENTED, WELL NOURISHED, NO ACUTE DISTRESS].
EYE: [PERRL, EOMI, NORMAL CONJUCTIVA].
HENT: [NORMOCEPHALIC, CLEAR TYMPANIC MEMBRANES, NORMAL HEARING, MOIST ORAL MUCOSA, NO SCLERAL ICTERUS, NO SINUS TEDERNESS].
NECK: [SUPPLE, NON-TENDER, NO CAROTID BRUITS, NO JVD, NO LYMPHADENOPATHY].
LUNGS: [CLEAR TO AUSCULTATION AND PERCUSSION, NON-LABORED RESPIRATION].
HEART: [NORMAL RATE, REGULAR RHYTHM, NO MURMUR, GALLOP OR EDEMA].
ABDOMEN: [SOFT, NON-TENDER, NON-DISTENDED, NORMAL BOWEL SOUNDS, NO MASSES].
MUSCULOSKELETAL: [NORMAL RANGE OF MOTION AND STRENGTH, NO TENDERNESS OR SWELLING].
SKIN: [SKIN IS WARM, DRY AND PINK, NO RASHES OR LESIONS].
NEUROLOGIC: [AWAKE, ALERT, AND ORIENTED X3, CN II-XII INTACT].
PSYCHIATRIC: [COOPERATIVE, APPROPRIATE MOOD AND AFFECT].
INTAKE & OUTPUT
LAB RESULTS
DIAGNOSTIC RESULTS
ASSESSMENT/PLAN
1. ACUTE CHF
   ORDERED CARDIOLOGY CONSULT FOR [TONIGHT.] ⎯1504

⎯1502

NOTE DETAILS: PROGRESS NOTE – GENERIC, GIF...

SIGN/SUBMIT | SAVE | SAVE & CLOSE | CANCEL

1500

NOTE COPY DETECTION

SIMILARITIES HIGHLIGHTED | HIGHLIGHT DIFFERENCES | MATCH TYPE: WORD ▼ | MATCH LENGTH: 5 ▼ 1716

PROGRESS NOTE  2012-10-07 09:23:00   1702

PATIENT: DOE, JOHN  MRN: 99-99-99-99-9  FIN: 0123456789
AGE: 52 YEARS  SEX: MALE  DOB: 02/26/1960
ASSOCIATED DIAGNOSES: NONE
AUTHOR: SMITH MD, ANN

VISIT INFORMATION
HOSPITAL ADMISSION DATE/TIME: 10/01/12 14:20
(HOSPITAL DAY NUMBER: 6) ~1706
CURRENT LOCATION: MEDICINE UNIT

SUBJECTIVE
HISTORY LIMITATION: NONE
CHIEF COMPLAINT: SHORTNESS OF BREATH

PATIENT WAS SEEN AND EXAMINED AT THE BEDSIDE THIS MORNING. *HE WAS SLEEPING WHEN INITIALLY SEEN AND WAS DROWSY DURING THE INTERVIEW. HE DENIED ANY CHEST PAIN, ABDOMINAL PAIN, NAUSEA, VOMITING. HE DIDN'T HAVE ANY FEVER OR CHILLS. HE HAD A BOWEL MOVEMENT THIS MORNING. HIS COUGH IS GETTING BETTER THOUGH HE STILL BRINGS UP WHITISH PHLEGM.* ⎬ 1708

OBJECTIVE

PROGRESS NOTE  2012-10-08 17:52:00   1704

PATIENT: DOE, JOHN  MRN: 99-99-99-99-9  FIN: 0123456789
AGE: 52 YEARS  SEX: MALE  DOB: 02/26/1960
ASSOCIATED DIAGNOSES: NONE
AUTHOR: SMITH MD, ANN

VISIT INFORMATION
HOSPITAL ADMISSION DATE/TIME: 10/01/12 14:20
(HOSPITAL DAY NUMBER: 7) ~1710
CURRENT LOCATION: MEDICINE UNIT

SUBJECTIVE
HISTORY LIMITATION: NONE
CHIEF COMPLAINT: SHORTNESS OF BREATH

PATIENT WAS SEEN AND EXAMINED AT THE BEDSIDE THIS MORNING.

OBJECTIVE
VS/MEASUREMENTS: VITAL SIGNS (MIDNIGHT YESTERDAY TO CURRENT)
PARAMETER LAST CHARTED MINIMUM MAXIMUM
PAIN SCORE 0  *(10/08 14:00)*
SPO2 96  *(10/08 14:00)*  ⎬ 1712
MBP 120/68  *(10/08 14:00)*

*FIG. 17.*

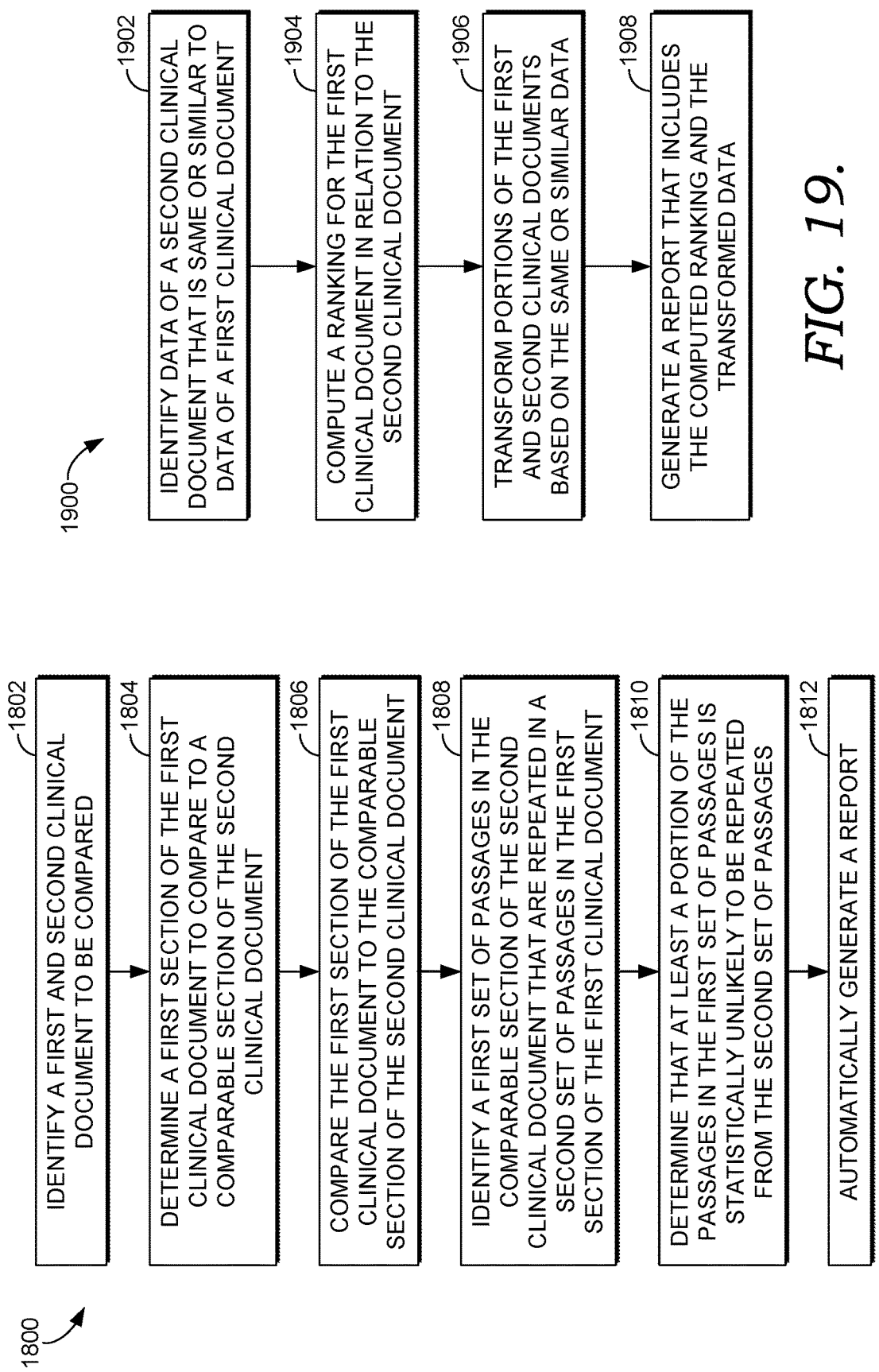

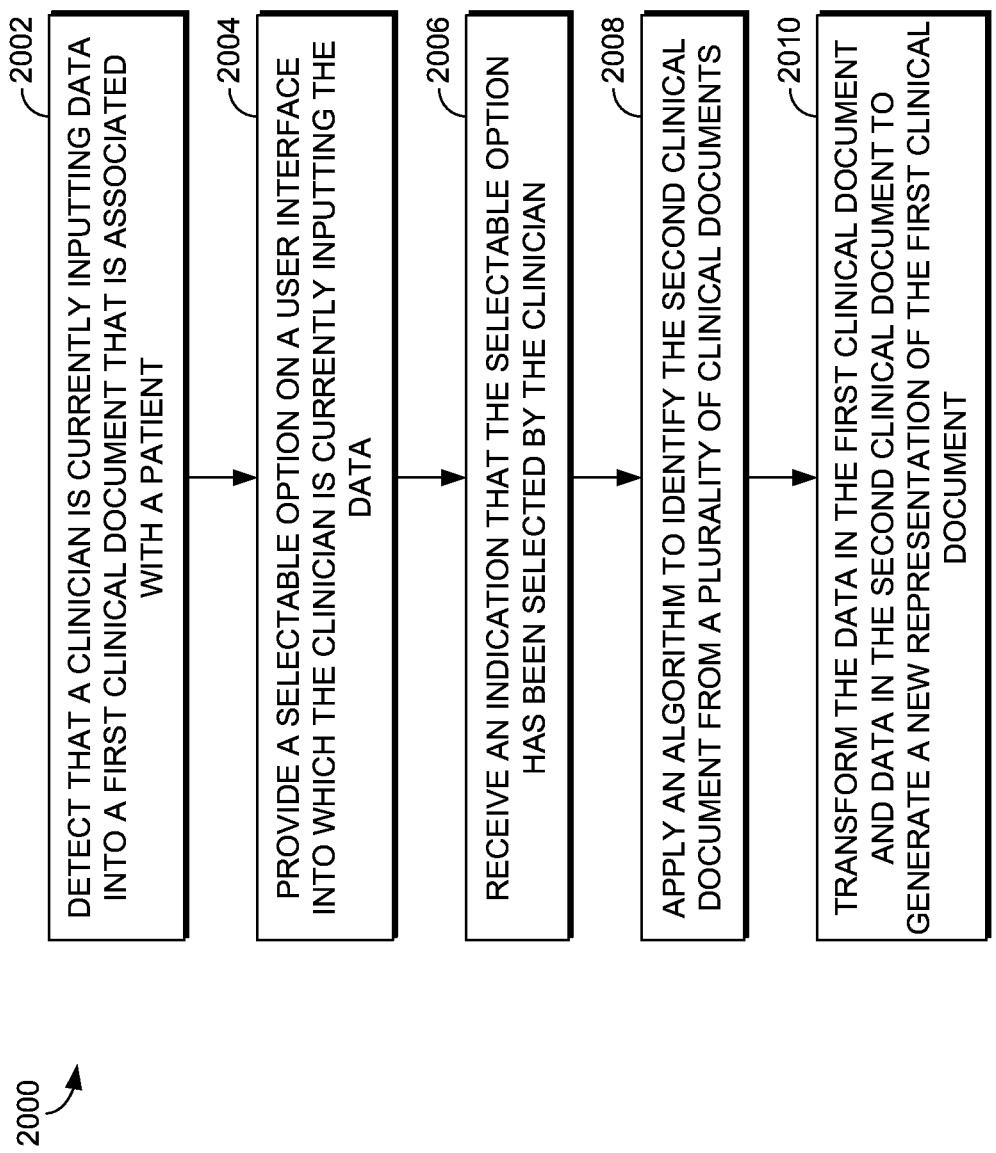

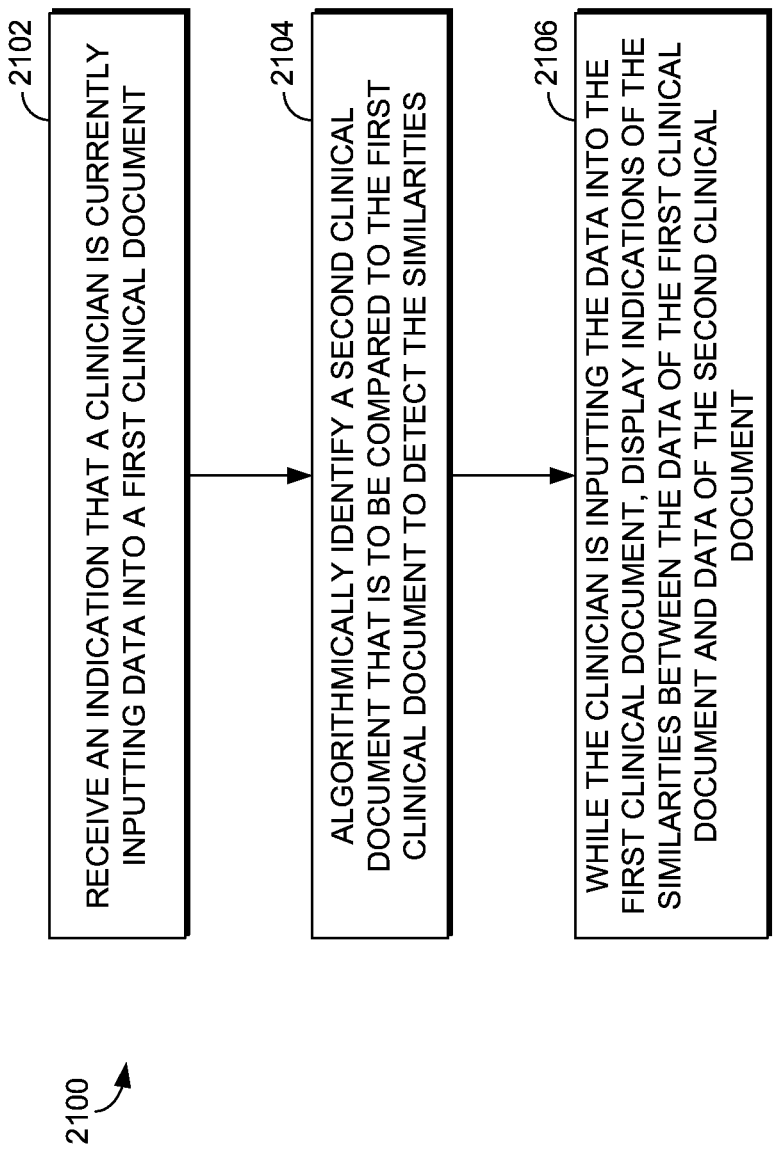

US 11,250,956 B2

DUPLICATION DETECTION IN CLINICAL DOCUMENTATION DURING DRAFTING

CROSS-REFERENCE TO RELATED APPLICATIONS

This application entitled "DUPLICATION DETECTION IN CLINICAL DOCUMENTATION DURING DRAFTING" claims priority to U.S. Provisional Patent Application No. 62/074,416, entitled "DUPLICATION DETECTION IN CLINICAL DOCUMENTATION," filed on Nov. 3, 2014, and is related by subject matter to concurrently filed U.S. Patent Application No. 62/074,416, entitled "DUPLICATION DETECTION IN CLINICAL DOCUMENTATION," and U.S. patent application Ser. No. 14/587,853, entitled "DUPLICATION DETECTION IN CLINICAL DOCUMENTATION TO UPDATE A CLINICIAN." The entireties of the aforementioned applications are incorporated by reference herein.

BACKGROUND

The accuracy of patient care records is important to many facets of a patient's care, including the quality of care and billing. When a clinician documents a service, such as a visit with a patient, the clinician may copy the contents of a previously-written clinical document as a starting point. While improving the clinician's efficiency in drafting the clinical document, this can lead to a variety of issues, such as intentional or unintentional duplication of portions of the previously-written clinical document that do not apply to the current encounter or service. If care is not taken, incorrect information may be entered into a clinical document in cases where the duplication carries forward information that is not corrected or amended. This can lead to confusion, errors, or billing inaccuracies.

Additionally, clinical documents can be lengthy, and thus it would take a clinician a significant amount of time to manually compare two clinical documents to one another either for the purpose of determining similarities between documents or to catch up on a patient's care. This is especially the case when large quantities of documents are to be compared to one another for auditing purposes. Even further, while the clinician is drafting a clinical document, it would be nearly impossible for a clinician to manually compare that clinical document to other clinical documents.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments are directed to systems and methods for detecting duplication in various portions of clinical documents. While some duplication is expected, such as a patient's health history, other duplication is not expected, which may include portions of a clinical document that refer to current aspects of a patient's care. In aspects herein, specific portions of a document that are determined to have a low likelihood of duplication are identified. These identified portions are compared to similar portions of other documents to determine whether duplication has occurred. In some aspects, the similar portions are evaluated to identify passages where inaccurate or inappropriate documentation might be present. In some aspects, a score or summary may be assigned to a particular document, reflecting the degree to which it may contain inaccurate or inappropriate information. This could occur after the current clinical document has been drafted, or while a clinician is drafting the clinical document, which provides a real-time analysis of that clinical document.

BRIEF DESCRIPTION OF THE DRAWINGS

Embodiments are described in detail below with reference to the attached drawing figures, wherein:

FIG. 3 is a chart that describes functional capabilities of a document comparison system, in accordance with an embodiment herein;

FIG. 4 is a comparison of two clinical documents with similarities indicated, in accordance with an embodiment herein;

FIG. 5 is a comparison of two clinical documents with differences indicated, in accordance with an embodiment herein;

FIG. 6 is an audit report detailing a comparison of multiple clinical documents, in accordance with an embodiment herein;

FIG. 7 is an exemplary screenshot of a user interface displaying a clinical document, in accordance with an embodiment herein;

FIG. 9 is an exemplary screenshot of a user interface displaying a first clinical document and a second clinical document, in accordance with an embodiment herein;

FIG. 10 is an exemplary screenshot of a user interface displaying a first clinical document and a second clinical document, wherein the user is selecting a new document for comparison, in accordance with an embodiment herein;

FIG. 11 is an exemplary screenshot of a user interface displaying a first clinical document and a third clinical document, in accordance with an embodiment herein;

FIG. 12 is an exemplary screenshot of a user interface displaying an indication of similarities between two clinical documents, in accordance with an embodiment herein;

FIG. 13 is an exemplary screenshot of a user interface displaying a clinical document having an option for a uniqueness score, in accordance with an embodiment herein;

FIG. 14 is an exemplary screenshot of a user interface displaying a clinical document having a uniqueness score, in accordance with an embodiment herein;

FIG. 15 is an exemplary screenshot of a user interface displaying an indication of statistically improbable similarities in two clinical documents, in accordance with an embodiment herein;

FIG. 17 is an exemplary screenshot of a user interface displaying an indication of differences between two clinical documents, in accordance with an embodiment herein;

FIGS. 18-22 are flow diagrams of methods of detecting similarities between clinical documents, in accordance with embodiments herein.

DETAILED DESCRIPTION

Figure 1:
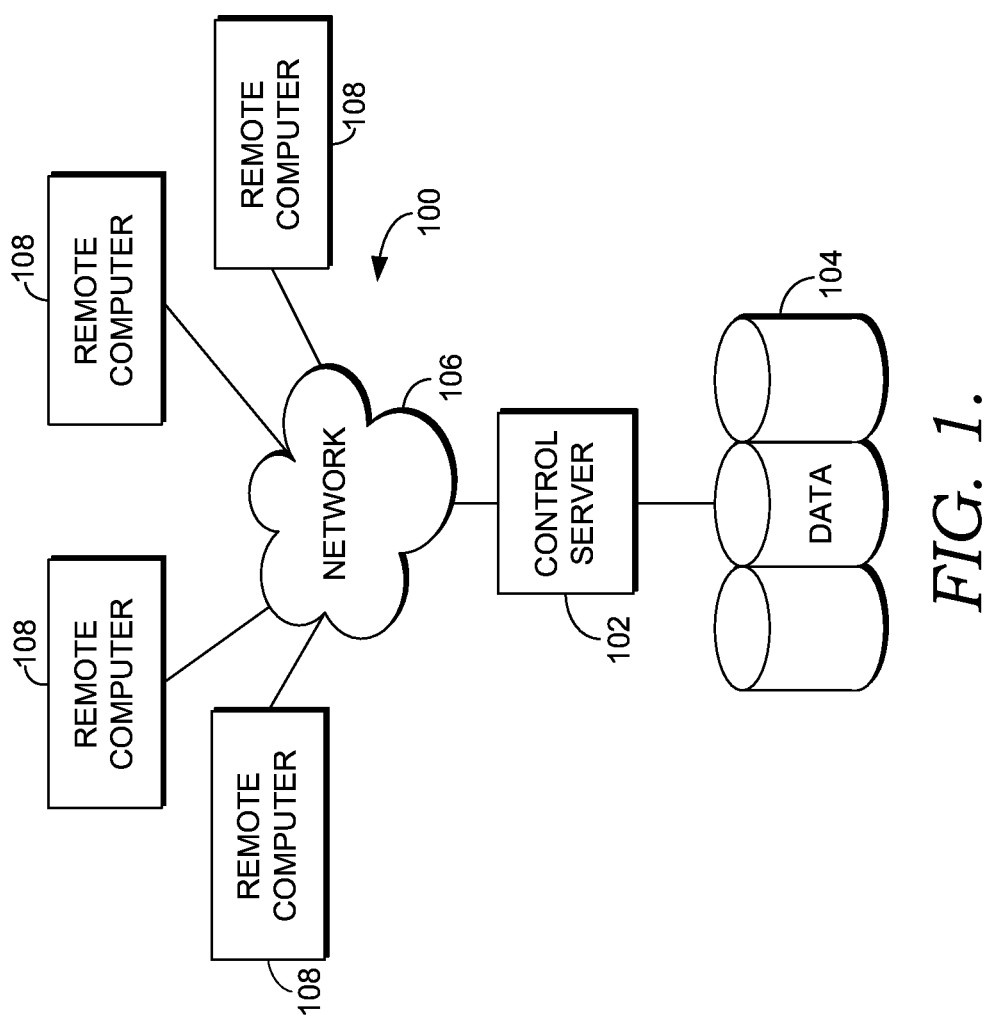
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Clinical documentation provides a narrative of care for patients as well as a means of documenting work to justify reimbursement from payers. Documentation is updated by various providers at different points in the care process, with each interaction often resulting in a new document or note. During the documentation process, providers may take actions to cause text to be duplicated from one note to another. For instance, they may use normal documentation templates which they modify to capture actual examinations and findings, or they may use a copy and paste function within an application to copy forward segments of text from one note into a new note in an effort to save typing. The copied information must then be reviewed, and updated to reflect the current care. If care is not taken, incorrect information can be put into a clinical note. This can lead to confusion, errors or billing inaccuracies.

The copying process can help to enable lengthy notes. These may include large amounts of duplicated text for completeness, and only small changes from note to note. When these clinical notes are viewed, clinicians attempting to find out "what changed" or "what's new" may have difficulty identifying those small, but important changes. Embodiments herein provide a means of detecting inappropriate duplication at scale (for auditing and reporting purposes) and at the individual document level. Embodiments herein also provide a means of detecting and displaying similarities or differences between a clinical document and a predecessor document to improve comprehension during the viewing process.

A clinical repository may contain tens of millions of clinical documents. To detect duplication, the system must compare documents with each other in order to find occurrences of duplication. For a repository with 20 million documents, for instance, theoretically one could perform 400 trillion comparisons, which is a massive undertaking even in today's big data computing era. Therefore, it is necessary to reduce the scope of detection to just those comparisons likely to result in duplication and to reduce the computational cost of a comparison.

Furthermore, the nature of duplication is such that sentences, paragraphs and sections may be copied to arbitrary locations within a new document, making comparisons using traditional sequentially oriented "diff" tools inadequate, as they are intolerant of many of these kinds of positional differences and rearrangements that may occur. So our comparison technique must be capable of adapting to such variation.

One exemplary approach to this may include controlling the number of comparisons performed. Embodiments permit comparisons to be limited to either a patient or provider axis. Within the patient axis, comparisons are limited to notes within a single patient's record, serially, with comparisons only being made between source notes and target notes for a given patient, where the date of service of the source note is earlier than or the same as the date of service of the target note. Similarly, notes that a provider has authored, without regard to the patient it was authored for, may be used as a source and target of comparison, where the source note was created with a service or publishing date prior to or equal to the service or publish date of a target note. Comparisons of clinical documents authored by the same clinician or provider for different patients could potentially avoid cases where a clinician is in a hurry to write a note and either intentionally or unintentionally copies text from a previous note from a different patient.

As mentioned herein, embodiments provide for identifying target documents of interest (e.g., a first clinical document to be compared to some other document), and then selecting predecessor documents, such as source documents, to which the target documents are compared. The selection of the source documents could be based on a number of factors, including, but not limited to, document type (e.g., only appropriate document types for comparison to the target are considered), date, location, encounter, subject, and author. Other factors may also be considered for selection of the source document (e.g., the second clinical document that is compared to the first clinical document).

In some embodiments, inappropriate repetition in an individual section of a clinical document may be evaluated by a textual match, such as whether the section is identical or similar in both documents. Also, inappropriate repetition may be evaluated by taking into account content of the section and the length of the section. For instance, if the repeated portion includes sentences that are very common or clinically unremarkable (stereotypic clinical "boilerplate," standard "normal" documentation produced by template, etc.), then the section's inappropriate repetition score may be reduced. Further, a lengthy section that is unchanged from the previous document represents more inappropriate repetition than a short, single-sentence section. Further, specific sentences or phrases may be identified that, if repeated from day to day, are particularly sensitive. These may be particularly indicative of possible incorrect documentation. In some cases, they are chosen because they are significant for clinical care, charges for care, or the clinical record.

Specifically, a number of features contribute to the scoring of document similarity. These features include: text similarity measures using a distance method (e.g., Jaccard distance, cosine distance, etc.), (Distance measure of sets comprised of an identical method of a sampling, or inclusion of all, character or word n-grams of the complete text of the documents being compared), (Distance measure of sets comprised of an identical method of a sampling, or inclusion of all, character or word n-grams of the text of a subset of clinical sections of the text of the documents being compared), (Distance measure of sets comprised of an identical method of a sampling, or inclusion of all, character or word n-grams of the text of a subset of clinical sections of the text of the documents being compared with statistically common phrases removed from the text of these sections); presence of identical sections of interest between the two documents (e.g., "Interval History section is identical"); count of identical sentences or phrases found in both documents which contain patterns drawn from a collection of temporal patterns (e.g., "Day X of antibiotics," "Staples were removed yesterday"); count of identical "statistically improbable sentences," or sentences that occur infrequently with respect to the corpus of clinical documents as a whole; count of identical sentences or phrases found in both documents which contain charge-related patterns drawn from a collection of charge-related patterns (e.g., "30 minutes spent counseling"); and count of phrases describing clinical procedures or occurrences that are unlikely to repeat from day-to-day (e.g., "surgical staples removed," "central line inserted," "medication dose increased to 40 mg"). The examples provided herein are also referred to as elements. In one embodiment, elements, such as specific temporal phrases, direct patient quotes, and other phrases that are statistically more or less likely to occur in multiple clinical documents, may be used to score or otherwise weight various documents to one another. The presence of certain duplicate features in the text, such as the examples of elements provided above, may cause the similarity score of a document to be higher or lower, based on which elements are present.

Embodiments provided herein enable duplication detection between two or more clinical documents. This assists to improve the quality of clinical documents. In one aspect, duplication detection may be used after a clinical document has been drafted. For example, as a tool for auditing the quality of clinical documents, aspects herein can be used to compare two or more clinical documents and to provide a score that indicates how similar the clinical documents are to one another. In some aspects, not all portions of a clinical document are compared to another clinical document. Embodiments provide methods for first determining which sections of a clinical document are not likely or should not have duplications, and just these sections are compared to one another. The score that is assigned to a particular document could be based on a text similarity measurement, a quantity of identical phrases or sentences having temporal patterns, a quantity of identical phrases or sentences that are statistically improbable to be repeated, a quantity of identical phrases or sentences having charge-related patterns, a quantity of phrases or sentences describing clinical procedures or occurrences that are unlikely to repeat from the first point in time corresponding to the first clinical document to the subsequent point in time corresponding to the second clinical document, or a combination thereof. For example, different sections of a document may be weighted differently, which may contribute to the overall score (indicate how similar a document is to another document) of a document. Further, certain elements in multiple documents having similarities that are potentially problematic can also be used to rate or score the documents as being more or less similar. Some of these elements include specific temporal phrases, direct patient quotes, and other phrases that are statistically more or less likely to occur in multiple clinical documents.

As mentioned, some embodiments are provided to detect and report passages in a clinical document that might be inaccurate or inappropriate. Documents inspected by the system may be limited to a single document, all documents related to a single patient or provider in a defined time interval, or the system may examine a very large set of documents, such as when auditing all clinical documents produced at a facility over a defined time period. The system operates by comparing a clinical document (the target document) to a similar, previous clinical document (the source document). This comparison detects similar passages in the latter, or target, document, and the previous, or source, document. These similarities are evaluated by a series of algorithms to identify passages that might be inaccurate or inappropriate. In particular, the system is able to detect inappropriate documentation that may have arisen as the result of text copied from a previous clinical document by the author. A report may then be generated without human intervention, the report indicating, at least, the possibly inappropriate similarities between the target document and source document.

Another embodiment may also provide a score or ranking as detailed above, but may occur while a clinician is drafting a clinical document. This may be useful for the drafting clinician to ensure that inappropriate portions of another clinical document, such as the previous clinical document available for the same patient, are not being duplicated. For example, the clinician may unintentionally copy a portion of the previous clinical document that states that the patient was "admitted to the ER this morning." Because this likely didn't happen two days in a row, this phrase could be flagged and could be brought to the clinician's attention. This would assist the clinician in drafting higher quality patient records, thus contributing to better overall patient care.

Still yet another embodiment is directed to duplication detection, but is used when a clinician needs to catch up on a patient's care. This could occur when the clinician is new to treating the particular patient, or it could occur when it has been a few days since the clinician saw the patient. Multiple clinicians could be involved in the treatment of a patient, and so it would be beneficial for a clinician to be updated to know what has been happening with the patient's care (other medications the patient is taking, improvements made, etc.). In this case, the system could determine which two documents to compare, or the clinician could make this selection. The system would then compare relevant portions of the two clinical documents and would provide indications of any differences or similarities between the two clinical documents. In one instance, the two clinical documents could have been drafted on two subsequent days, thus showing any improvements the patient has made. In some embodiments, buttons may be provided on a user interface that allow the clinician to compare other clinical documents, such as comparing a current clinical document to a previous clinical document so that the clinician can compare a first clinical document from a first day to a second clinical document from a second day, then select to compare the second clinical document from the second day to a third clinical document from a third day, etc. This would allow the clinician to move forward or backwards. In one instance, a clinician could use the embodiment described above when the clinician is new to a case or wants to review the chart or determine when a particular event occurred, such as when a drug dose was changed, on which day the patient first got out of bed after surgery, etc.

In embodiments, the algorithm used to make the comparison between two or more clinical documents may flex, or be modified, based on various factors. For instance, the algorithm may flex based on the institution (e.g., client preferences or style of practice), a document type (e.g., inpatient daily progress note may be evaluated differently than a discharge summary or an outpatient clinic visit document), patient care or condition or provider specialty (e.g., different rules might apply for hospitalized psych patient without other medical problems, than for postsurgery patient with extensive medical problems, or the like. Further, various aspects of the algorithm may flex, including a similarity indicator (e.g., the threshold that determines the "severity" level of indicator), a visual representation of the similarity indicator severity (color, icons, etc.), a visual representation of similarity, sections of the document to evaluate and criteria for evaluating them, specific identical phrases and sections to be evaluated, such as "statistically improbable," "charge-related," "describing clinical procedure or occurrences," "temporal patterns," or the like, etc.

As such, a first exemplary aspect is directed to one or more computer-readable media having computer-executable instructions embodied thereon that, when executed by a computing device, perform a method of detecting similarities between two or more clinical documents. The method includes detecting that a clinician is currently inputting data into a first clinical document that is associated with a patient, and providing a selectable option on a user interface into which the clinician is currently inputting the data, wherein the selectable option, if selected, causes an indication of similarities between the first clinical document and a second clinical document to be provided. The method further includes receiving an indication that the selectable option has been selected by the clinician, applying an algorithm to identify the second clinical document from a plurality of clinical documents. The second clinical document is identified to be compared to the first clinical document. Further, the method includes transforming at least a portion of the inputted data in the first clinical document and at least a portion of data in the second clinical document to generate a new representation of the first clinical document that indicates at least a portion of the similarities between the first clinical document and the second clinical document.

A second exemplary aspect is directed to one or more computer-readable media having computer-executable instructions embodied thereon that, when executed by a computing device, perform a method of detecting similarities between two or more clinical documents. The method includes receiving an indication that a clinician is currently inputting data into a first clinical document, and algorithmically identifying a second clinical document to which at least a portion of the inputted data of the first clinical document is to be compared to detect the similarities. The algorithmically identifying is based on one or more of times associated with the first clinical document and the second clinical document, an identity of one or more clinicians who authored the first and second clinical documents, an identity of one or more patients associated with the first and second clinical documents, a type of the first clinical document, or contents of the first clinical document. Further, while the clinician is inputting the data into the first clinical document, the method also includes displaying indications of the similarities between the data of the first clinical document and data of the second clinical document.

A third exemplary aspect is directed to a system for detecting similarities between two or more clinical documents. The system includes one or more processors and one or more computer storage media storing computer-useable instructions that, when used by the one or more processors, cause the one or more processors to perform a series of method steps. The method steps include determining that a user is currently inputting data into a first clinical document associated with a patient, and from at least one database storing a plurality of clinical documents, identifying a second clinical document to which the first clinical document is to be compared. The method also incudes, in real time, comparing at least one portion of the first clinical document to at least one comparable portion of the second clinical document, and dynamically presenting a real-time similarity indicator that indicates to the user how similar the at least the one portion of the first clinical document is to the at least one comparable portion of the second clinical document.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

Embodiments provided herein might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments provided herein might be described in the general context of computer-executable instructions, such as program modules, being executed by a computer. Exemplary program modules comprise routines, programs, objects, components, and data structures that perform particular tasks or implement particular abstract data types. The embodiments provided herein might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102 and includes volatile and nonvolatile media, as well as removable and nonremovable media. By way of example, and not limitation, computer-readable media may comprise non-transitory computer storage media and communication media. Computer storage media includes both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physician's assistants; nurse practitioners; nurses; nurse's aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
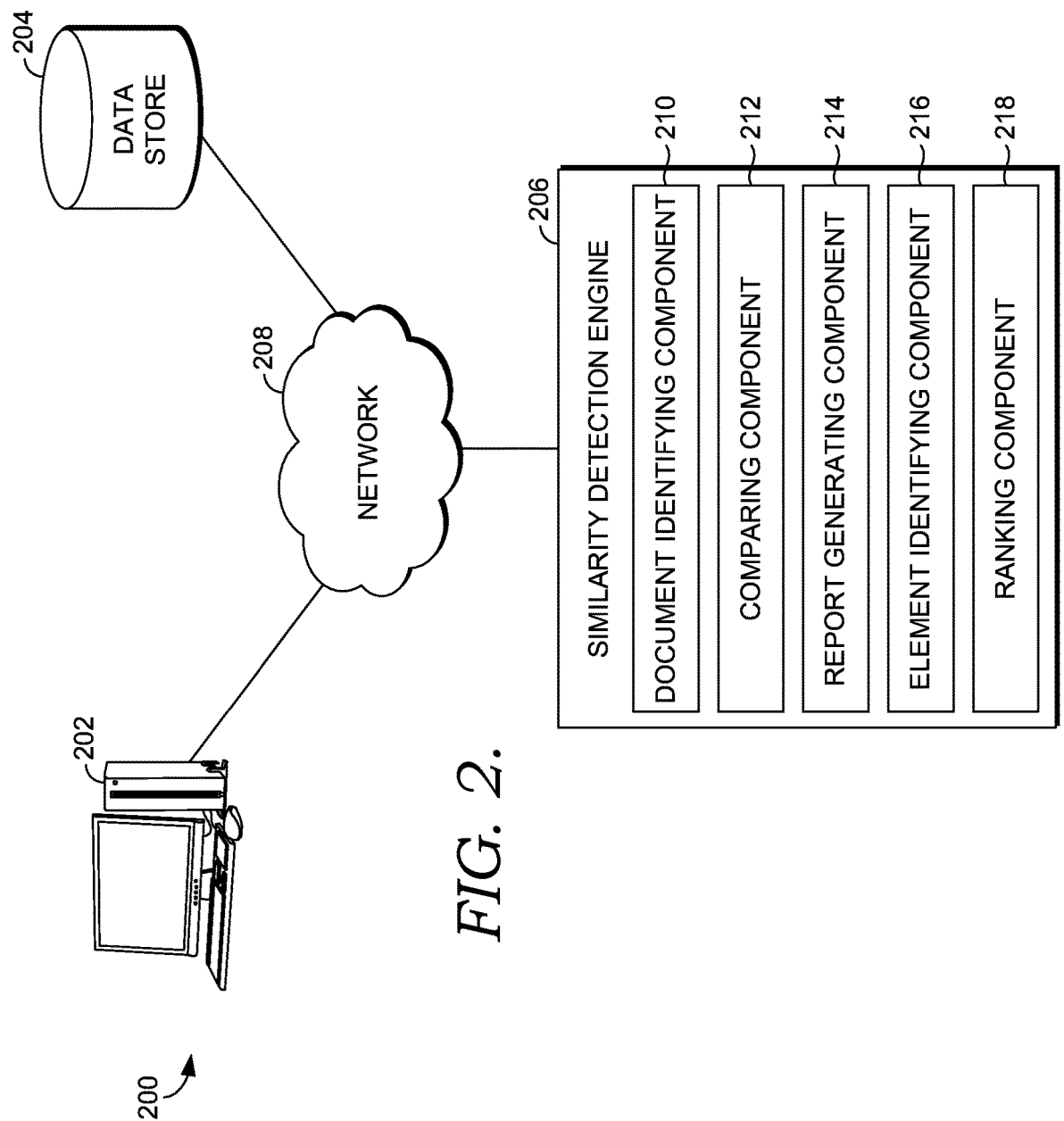
FIG. 2 is a block diagram of an exemplary system for carrying out embodiments of the present invention.

Turning now to FIG. 2, a block diagram 200 is illustrated, in accordance with an embodiment of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown, the system 200 may include a computing device 202, a data store 204, and a similarity detection engine 206. These components may communicate with one another by way of network 208. Network 208 may comprise local area networks (LANs) and/or wide area networks (WANs). The computing device 202 may function, in some embodiments, to receive input from one or more users, such as clinicians. For instance, while a single computing device 202 is illustrated in system 200, a plurality of computing devices may actually be utilized in system 200. For example, in a hospital or other medical care facility, many computing devices are typically used that can be shared by the users in those facilities. A single user may not use the same computing device each time a clinical document or some other document is edited.

The computing device 202 may be used in embodiments herein to allow a clinician who is currently inputting data into a clinical document to understand how similar that document is to other documents. Alternatively, the computing device 202 may be used by a hospital administrator, auditor, manager, etc., to generate a report that indicates how similar a clinical document is to at least one other clinical document, such as a clinical document authored by the same user, or a clinical document corresponding to the same patient. Even further, the computing device 202 may be used to assist a user, such as a nurse or a doctor, to catch up on a particular patient's care. For example, the clinician attending to the patient may not have seen or treated the patient in several days and may want to catch up on what has happened with the patient since that time. Embodiments described herein allow the clinician to compare clinical documents to easily ascertain what is different in each of the clinical documents and, as such, what has been happening with the patient since the clinician last saw the patient. Still yet, the clinician may be new to the case and may not have ever seen or treated the patient. A comparison of multiple clinical documents would allow the clinician to catch up in an efficient manner.

The data store 204 stores clinical documents for a plurality of patients. The data store 204 may store documents only for a particular location of a healthcare facility, or for multiple locations of healthcare facilities. The clinical documents stored therein may include progress notes, clinic notes, discharge summaries, oncology reports, therapist notes, rehabilitation notes, or any other document with patient information authored by a user, such as a clinician. As used herein, a clinician refers to any person who provides care for a patient. This could include any type of doctor, a nurse, a therapist, a physical therapist, an occupational therapist, etc.

As mentioned, the system 200 also includes a similarity detection engine 206. The similarity detection engine 206 is generally responsible for detecting similarities or even differences between two or more documents. The components of similarity detection engine 206 in system 200 may be utilized to compare at least two clinical documents that have already been created, such as to perform an audit on the documents to determine any inappropriate similarities between documents, or simply to provide a healthcare facility with information regarding how similar or different clinical documents are in relation to one another.

The components of the similarity detection engine 206 comprise a document identifying component 210, a comparing component 212, a report generating component 214, an element identifying component 216, and a ranking component 218. The document identifying component 210 is configured to identify one or more documents that are to be compared to other documents. In one instance, both the target and source documents (e.g., a first clinical document and a second clinical document) are identified by the document identifying component 210. The identification of the documents may be based on, for example, times associated with the documents (e.g., time of creation or authorship, time of editing), which clinicians authored the documents (e.g., do we want to compare documents created by the same clinician or by different clinicians but associated with the same patient), which patients are associated with the document, the type of the documents, contents of the documents, etc. For example, it may be desirable to compare two or more documents of the same type, such as a progress note, as these types of notes may typically include similar types of information. Or, it could be determined that two or more documents all include similar content, and that content is what is desired to be compared.

In one embodiment, a component of the system 200 may be used to identify a particular section of the documents for comparison, as it may not be desirable for the entirety of each document to be compared. While it may be typical for some sections of a clinical document to remain unchanged from day to day, other sections are more prone to change. For instance, sections with temporal patterns (e.g., sections that mention a time, a day, a time of a particular day) and sections that mention specific dosages of medication are likely to change from a first point in time to a second point in time, such as from day to day. An algorithm is trained to learn which sections of a particular clinical document have information that is statistically probably to change from a first point in time (associated with a first clinical document) to a second point in time (associated with a second clinical document). In one embodiment, a score or a ranking, as will be described herein, could be computed for a particular section instead of for an entire document, as a good portion of two documents corresponding to a single patient could be the same from day to day.

As mentioned, temporal rules could be used to identify a section of a clinical document that is statistically likely to change from one day to the next for a single patient. One example is the word "today" mentioned in a clinical document with a procedure that has already occurred. Other temporal mentions that the algorithm may look for include "this morning," "tonight," specific durations of time, a reference to a specific day, time relevant to an event, such as "days past surgery," when the patient was admitted to the hospital, or the like.

In one aspect, a component of the system 200 could be used to align various portions of the clinical documents prior to the portions being compared. As discussed, a first section of a first clinical document may be identified so that it can be compared to a comparable section of a second clinical document. In some instances, the first section and the comparable section may not be under the same section heading. Or the first section may be at the beginning of the first clinical document while the comparable section is at the end of the second clinical document, or vice versa. In any of these cases, it may be determined that portions of the documents that are similar, such as those that are describing something similar (e.g., history of the patient, medication dosages, when the patient was admitted to the hospital, how the patient is feeling that day), and may align them prior to the comparison.

In one aspect, algorithms used as described herein may first identify documents that are to be compared, normalize the text in the documents, determine where each section begins and where each ends, determine those sections that are important, and then perform the comparison of various portions of two or more documents. As such, the algorithms used may be insensitive to the arrangement of text in the clinical documents being compared.

The comparing component 212 is generally configured to compare at least a portion of a first clinical document to at least a portion of a second clinical document. As mentioned herein, a component of the system 200 may determine the portions or sections of a particular document that are to be compared to similar portions or sections of other documents. Once this is determined, the comparing component 212 performs a comparison of these sections. In some embodiments, the comparing component 212 compares the entirety of a first clinical document to the entirety of other clinical documents. The comparing component 212 may work along with an element identifying component 216. For instance, the element identifying component 216 may be configured to identify elements, also termed features, in the documents being compared that are unlikely to be repeated. As mentioned, these elements may include temporal elements, charge-based elements, identical phrases or sentences that are statistically improbable to be repeated, phrases or sentences describing clinical procedures or occurrences that are unlikely to repeat from the first point in time corresponding to the first clinical document to the second point in time corresponding to the second clinical document, and the like.

The comparison done by the comparing component 212 may include comparing, letter by letter or word by word, or rather a sliding window of groups of letters or words, where the window size is a parameter, the text of the first section and the similar section. In one embodiment, portions or sections of the documents being compared are not in the same location of each respective document, or may not be under the same section heading. Irrespective of this, the comparing component 212 has the capability to locate the comparable or similar sections for comparison. In one embodiment, for the sentence, "In one embodiment, the first section and the similar section are not in the same location of each respective document, or may not be under the same section heading," the comparing component 212 may do a character n-gram compare of size 7 that slices things up for comparison like this: "In one", "n one e", "one em", "one emb", "ne embo", etc. Alternatively, the passage comparing component 212 may do a word n-gram compare of size 7 that slices things up for comparison like this: "In one embodiment, the first section and", "one embodiment, the first section and the", "embodiment, the first section and the similar", etc.

A component of the system 200 may operate to identify a first set of passages in one of the documents being compared that is either the same or at least substantially similar (e.g., past a predetermined threshold of similarity) to a second set of passages in the other document. Here, at least a portion of the passages in the first set of passages is statistically unlikely to be repeated in the second set of passages.

The report generating component 214 is generally configured to automatically generate a report without human intervention. The report may indicate, at least, the similarities between the sections or portions of the two or more documents being compared. The report generating component 214, in embodiments, utilizes the passages found to be the same or similar in the at least two documents, such as the first and second clinical documents, and automatically generates a report without human intervention. The report generated by the report generating component 214 may include a score, a ranking, etc., as will be discussed further herein, and could also include an indication of the words or phrases that are the same or similar, and why they are unlikely to be the same from one day or time to another.

The similarity detection engine 206 also may include a ranking component 218 that is configured to compute a ranking or score for the elements or features that have been identified in the documents that are being compared, or may compute a ranking or score for a document, as it is compared to one or more other documents. As such, a ranking could be computed for just the first section of the first clinical document, or for the entire first clinical document as a whole. The ranking may indicate a relative risk of the first clinical document having inappropriate duplication from the second clinical document. In embodiments, the ranking may be based on at least one of a text similarity measurement, a quantity of identical phrases or sentences having temporal patterns, a quantity of identical phrases or sentences that are statistically improbable to be repeated, a quantity of identical phrases or sentences having charge-related patterns, or a quantity of phrases or sentences describing clinical procedures or occurrences that are unlikely to repeat from the first point in time corresponding to the first clinical document to the second point in time corresponding to the second clinical document. As used herein, temporal patterns are sequences of words that reference a particular day, a week, a time of day, etc. Charge-related patterns reference details of the clinician's visit with the patient, such as procedures performed.

FIG. 3 is a chart 300 that describes functional capabilities of a document comparison system, in accordance with an embodiment herein. The chart 300 illustrates that passages from a first clinical document (previous note) and passages from a second clinical document (a current or evaluated note) may be compared such that text similarity (e.g., significant similarities of elements) and text differences may be evaluated. In the row labeled "Text similarity," for example, a portion of an evaluated note is displayed and is in bold to indicate that the portion is the same as a previous note, but "80" is underlined, as it is different than the previous note. Similarly, for the row labeled "Features," the phrase "Admitted this a.m. from ED" in the evaluated note is bolded for being the same as in the previous note, but "Admitted this a.m." is also underlined for having a particular significance, which may indicate that it is statistically unlikely that a patient would have been admitted "this a.m." for consecutive times that notes were drafted. For document similarity score, one of a "high risk," a "low risk," or an "appropriate" score may be provided based on the similarities found between two or more documents.

Turning now to FIG. 4, a comparison 400 is illustrated of two clinical documents with similarities indicated, in accordance with an embodiment herein. Initially, it is noted that the comparison includes a first clinical document 404 and a second clinical document 406. As shown, the first clinical document 404 was created one day earlier than the second clinical document 406, so it is of interest to compare the two documents to determine how much, if any, of the second clinical document 406 is the same or similar to the first clinical document 404, which could indicate inappropriate copying from one document to another. In the embodiment of FIG. 4, the similarities between the documents are highlighted, indicated by area 402 of the user interface.

As shown, a good portion of the two documents have the same text. However, just because this amount of text seems to have been copied from the clinical document from the day before does not necessarily indicate inappropriate copying. As shown here, some of the sections of the documents, including the patient's name and a review of systems, may not be expected to change at all or much between two consecutive days. However, because the patient's cough is shown to have improved since the time the first clinical document 404 was created instead of being unchanged, this may indicate that the clinician copied a portion of the first clinical document 404 into the second clinical document 406 but clearly met with the patient and changed this portion of the document. Also, because one of the three medication dosages has changed in the second clinical document 406 from the first clinical document 404, this may indicate that the clinician did not inappropriately copy at least this section of the clinical document.

FIG. 5 is a comparison 500 of two clinical documents with differences indicated, in accordance with an embodiment herein. As shown, the first clinical document 504 and the second clinical document 506 are being compared, as they were in FIG. 4. However, here, the differences are highlighted instead of the similarities, as indicated by area 502 of the user interface. Whether differences or similarities are highlighted or otherwise indicated to the user may be a user preference that can be changed by the user to get the best comparison of two clinical documents. In the embodiments of both FIGS. 4 and 5, the user could be currently inputting data into a clinical document while the comparison is shown. As such, in one aspect, the clinical document into which the user is currently inputting text could be fully editable while the comparison is displayed.

Referring to FIG. 6, an audit report 600 is shown detailing a comparison of five clinical documents to previous clinical documents, in accordance with an embodiment herein. As shown here, the audit report 600 is a risk assessment for a particular clinical document. The audit report 600 identifies passages in the clinical document that, based on, for example, statistical measurements, should not remain the same for consecutive days. For example, for the first note 602, as shown in the "Comparison to Previous Note" column, two consecutive progress notes have the same sentence of "Greater than 30 minutes spent removing surgical staples today." There are two temporal clues in this sentence that could indicate that this sentence would likely not appear on two different days. First, the time it took to remove the stitches and that the stitches were removed "today." Additionally, because the note states that this is "Post-Op day 3," which was also the same in a previous day's notes, this particular note is graded as a high risk for being inappropriately copied. Some other examples of phrases that typically would not repeat from day to day include "Patient was admitted [today/yesterday/this a.m.]," "[Medication] dose increased to x today," and "Antibiotic day x."

For the second note 604, the grade given is also high risk for similar reasons as the first note 602. For example, while it is possible that the patient had intermittent nausea during the night and vomited twice for two nights in a row, this raises a flag in the system for potentially having been inappropriately copied from the previous note. For the third note 606, the grade given is a moderate risk. Again, because a day referred to in the note is the same day as was referred to in a previous note, there is a moderate risk that this may have been copied, whether intentional or not. Referring to the fourth note 608, the grade given is a moderate risk. While no specific passages are quoted in the "Comparison to Previous Note" column, it is shown that four separate sections of the note are unchanged from a previous note. In embodiments, the particular section that is unchanged is factored into the risk computed for a particular document. As mentioned, if the name of the patient and the patient's medical history remain unchanged, that is likely to be expected, whereas the plan for the patient's treatment or anything that occurred with the patient that day would likely not repeat from day to day. For the fifth note 610, the risk is lowered as a "possible risk" based on the sections that are unchanged and that the patient did not have cramping, which is a likely occurrence for two different days. As discussed, many factors may go into determining the risk of a clinical document having been inappropriately copied from a previously created clinical document. While some are mentioned here, other factors not mentioned specifically herein are also considered to be within the scope of embodiments herein.

Figure 7:
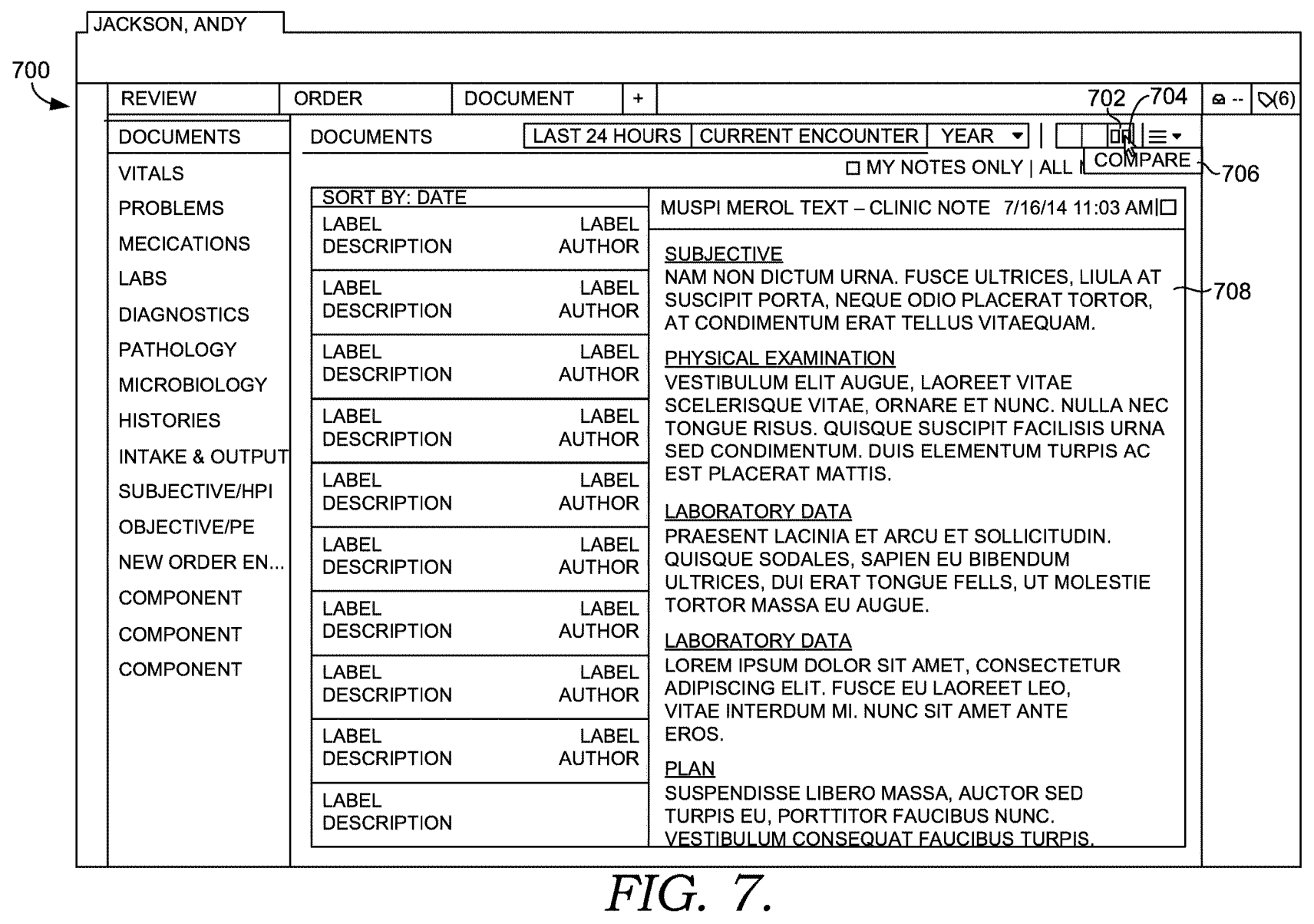

FIG. 7 is an exemplary screenshot 700 of a user interface displaying a clinical document 708, in accordance with an embodiment herein. FIGS. 7-11 will be described in conjunction with one another, showing a sequence of events that enable a user to compare two or more clinical documents. In FIG. 7, a compare button 702 is provided on the user interface. As shown, the cursor 704 is currently hovering over the compare button 702, which, in this embodiment, provides for the word "compare" 706 to appear on the screen. FIG. 7 is generally depicting how a user who is either currently inputting data into a document, or a user who has previously entered text into a document, is able to edit his or her own document by comparing it to previous documents. This may also be used by others in the healthcare facility, such as, for example, auditing clinical documents for similarities.

Figure 8:
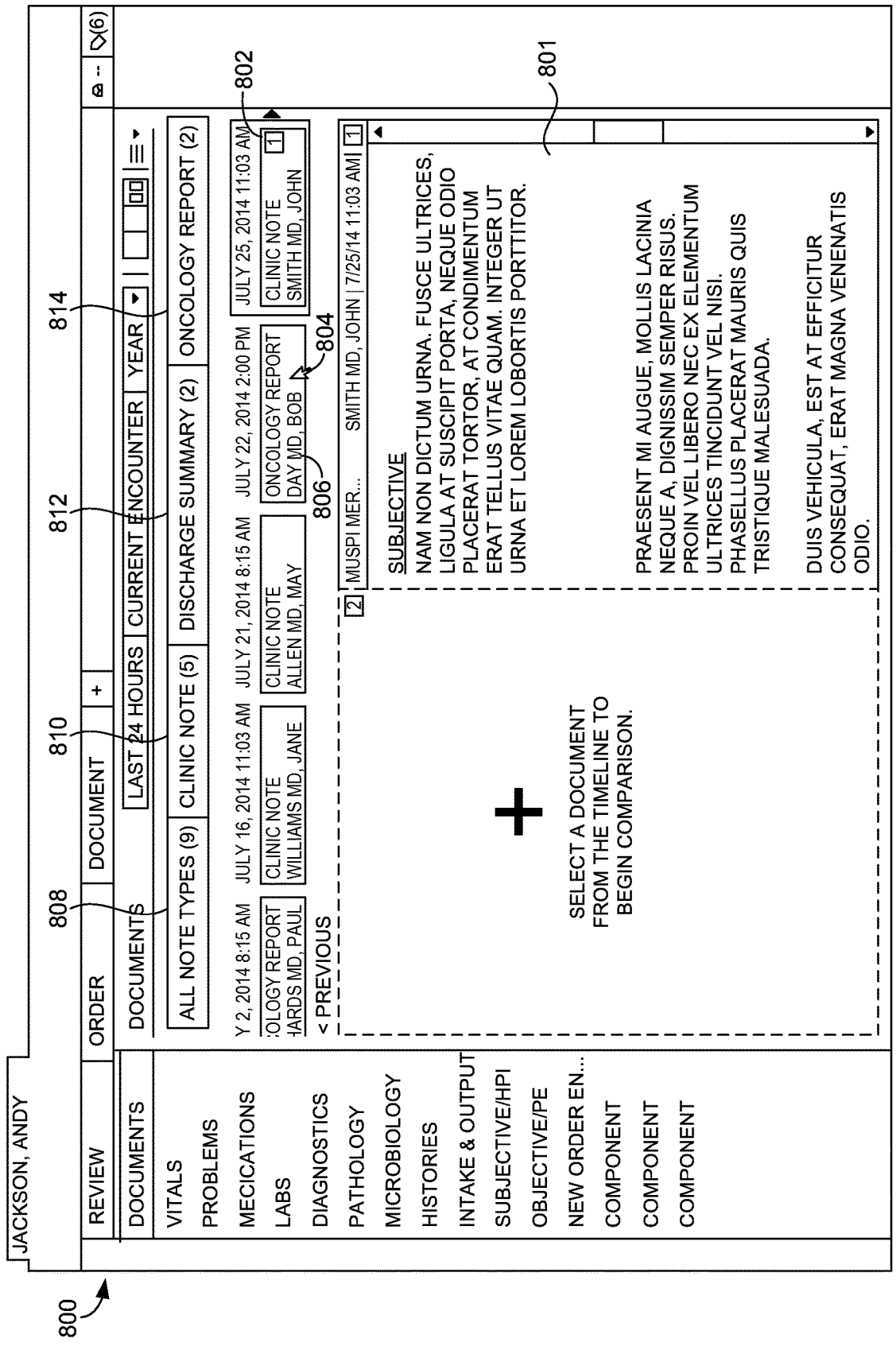
FIG. 8 is an exemplary screenshot of a user interface displaying a clinical document, the user interface allowing a user to compare a first clinical document to a second clinical document, in accordance with an embodiment herein.

FIG. 8 is an exemplary screenshot 800 of a user interface displaying a clinical document, where the user interface allows a user to compare a first clinical document to a second clinical document. As the user has previously selected the compare button 702, the user is now able to select a second clinical document with which to compare to the first clinical document. As shown, the first clinical document 801 in FIG. 8 corresponds to the clinical note 802 highlighted by being enclosed in a box. Both have the number 1 by them, indicating that they are the same document. As such, it is easy to determine which clinical document is currently being displayed on the user interface.

Multiple potential clinical documents are provided as options on the user interface, as well as others not shown as indicated by the arrow. The system may utilize an algorithm to identify these clinical documents from which the user may select. The algorithm may take into account, for example, the document type, the clinician who authored the first clinical document, the clinicians who authored the clinical documents that are provided as options for selection, the patient corresponding to the clinical documents, or the like. The algorithm may utilize more complicated factors when identifying potential clinical documents to which the first clinical document is to be compared. For instance, the content of the previous clinical documents may be analyzed to identify those that may have notes relating to the same symptoms, condition, etc., as the notes in the current or first clinical document. Particular sections may be analyzed in the previous clinical documents. If any of the previous clinical documents do not have a particular section that the first clinical document has, those may not be provided to the user for comparison purposes.

As shown in FIG. 8, the user is selecting clinical document 806, as shown by the cursor 804 over this selection. The user may decide that the first clinical document should be compared to a different type of document. For example, the user may select all note types 808, a clinic note 810, a discharge summary 812, or an oncology report 814.

Figure 9:
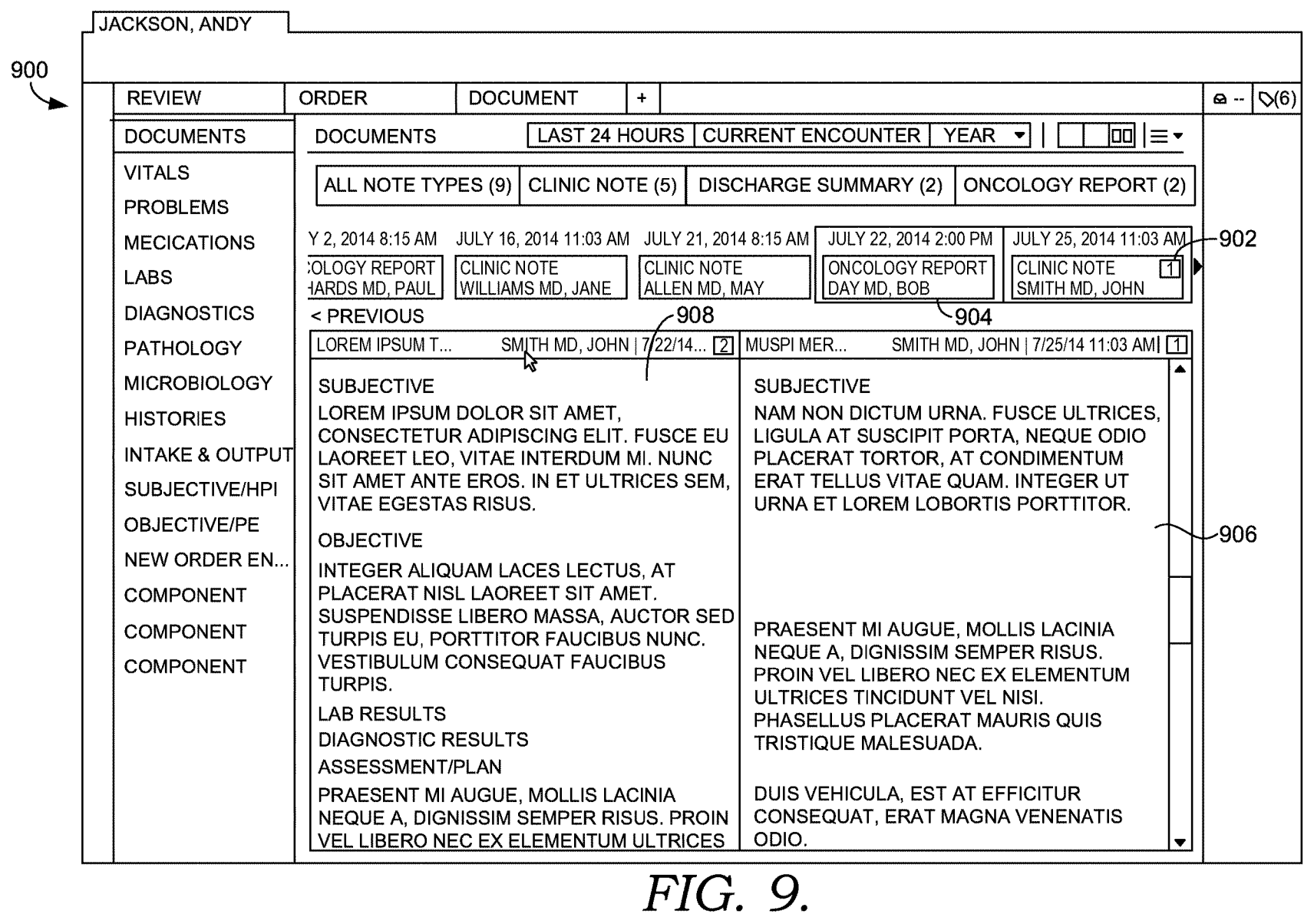
Figure 10:
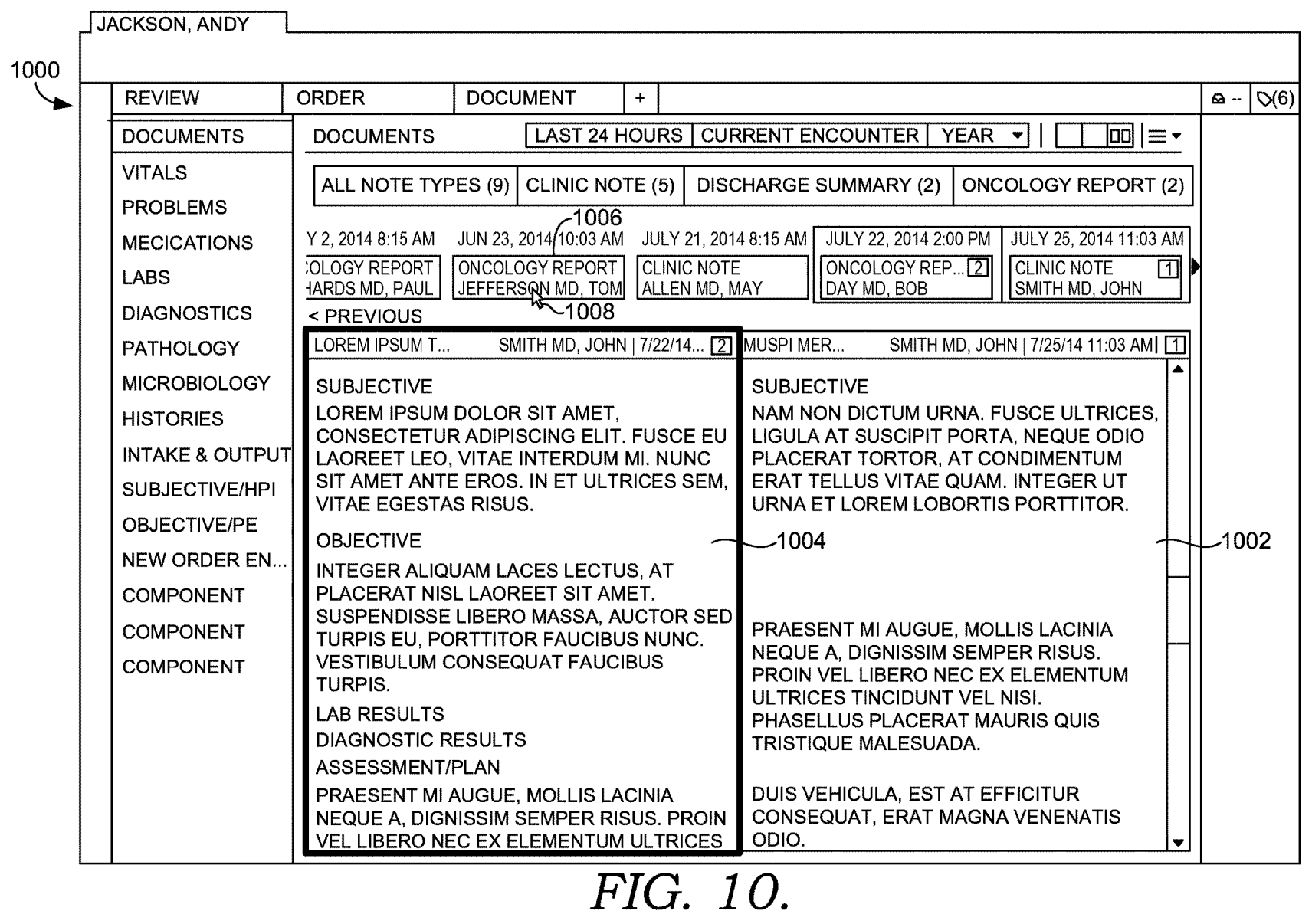

FIG. 9 is an exemplary screenshot 900 of a user interface displaying a first clinical document and a second clinical document. The first clinical document 906 may be compared to a second clinical document 908, both of which correspond to a clinical document selection button above, items 902 and 904, respectively. At the exemplary screenshot 1000 of FIG. 10, the user is selecting a different second clinical document to which the first clinical document 1002 is to be compared. As the display device previously displayed the first clinical document 1002 and the second clinical document 1004, the clinical document represented by clinical document button 1006 is now being selected, as indicated by the cursor 1008 over the clinical document button 1006. FIG. 11 then illustrates a screenshot 1100 of the previously displayed clinical document having been replaced by second clinical document 1104, corresponding to clinical document button 1102. FIG. 11 also shows that a user is attempting to change the note type with which to compare to the first clinical document. Here, the user is selecting, by way of cursor 1106, a clinic note button 1108.

Figure 12:
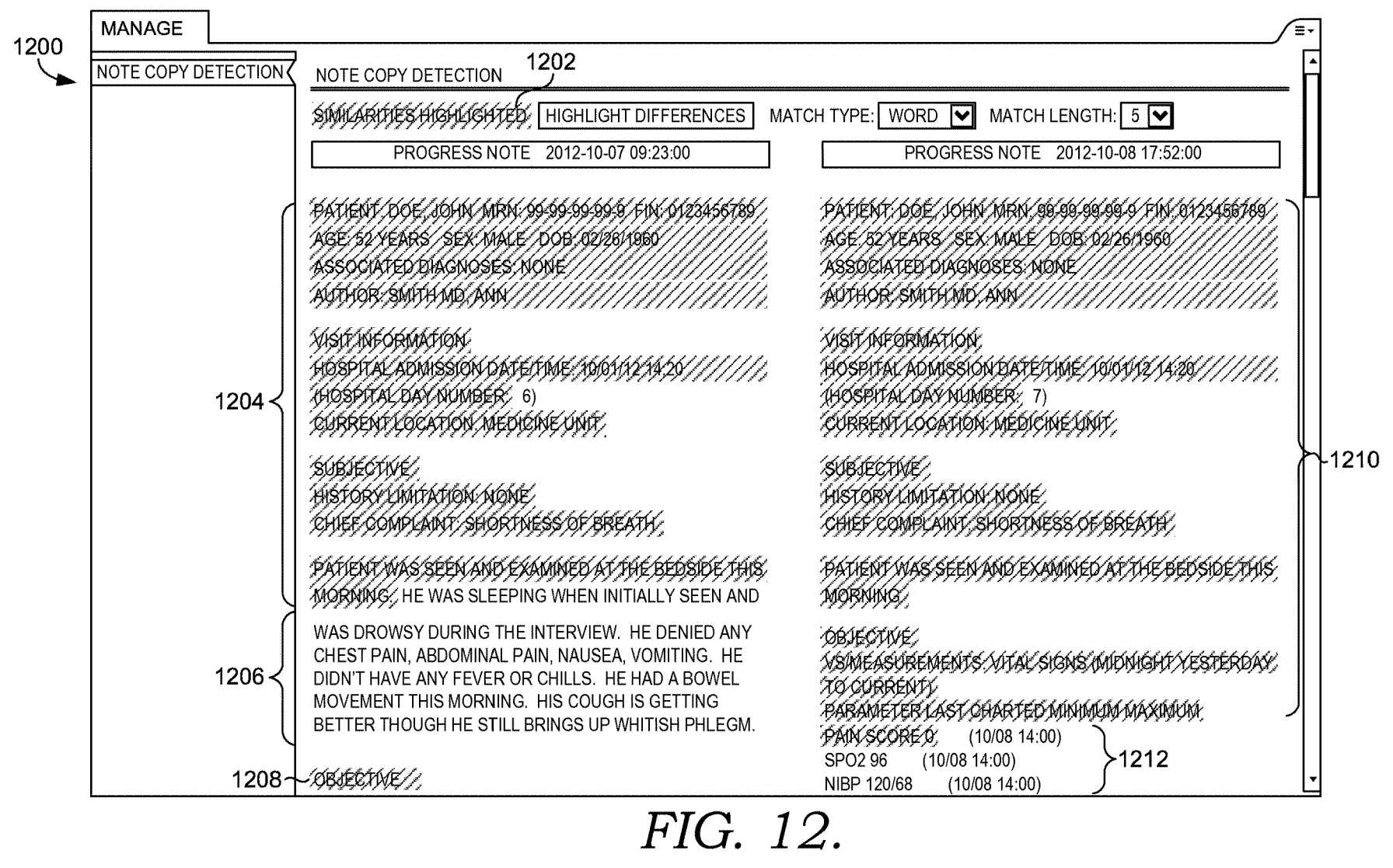

Turning now to FIG. 12, an exemplary screenshot 1200 of a user interface is shown displaying an indication of similarities between two clinical documents, in accordance with an embodiment herein. Here, the box labeled "similarities highlighted" 1202 has been selected by a user. As such, the user is requesting to view the similarities between the two clinical documents. Here, all similarities are highlighted in both documents. In the first clinical document, those portions that are the same in the two documents include portions 1204 and 1208, while portion 1206 is different. In the second clinical document, the portions that are the same in the two documents include portion 1210, while portion 1212 is different. This comparison of two documents could be done after both documents have been created and after the user has entered all text, or could be done while the user is inputting data into one of the documents. While FIG. 12 and other figures herein illustrate two documents on a single user interface display, it is contemplated that just one or more than two documents may be displayed simultaneously. For instance, once a comparison has been done between two or more documents, a new representation comprising annotations may be presented on the display to easily allow a user to determine the differences or similarities.

Figure 13:
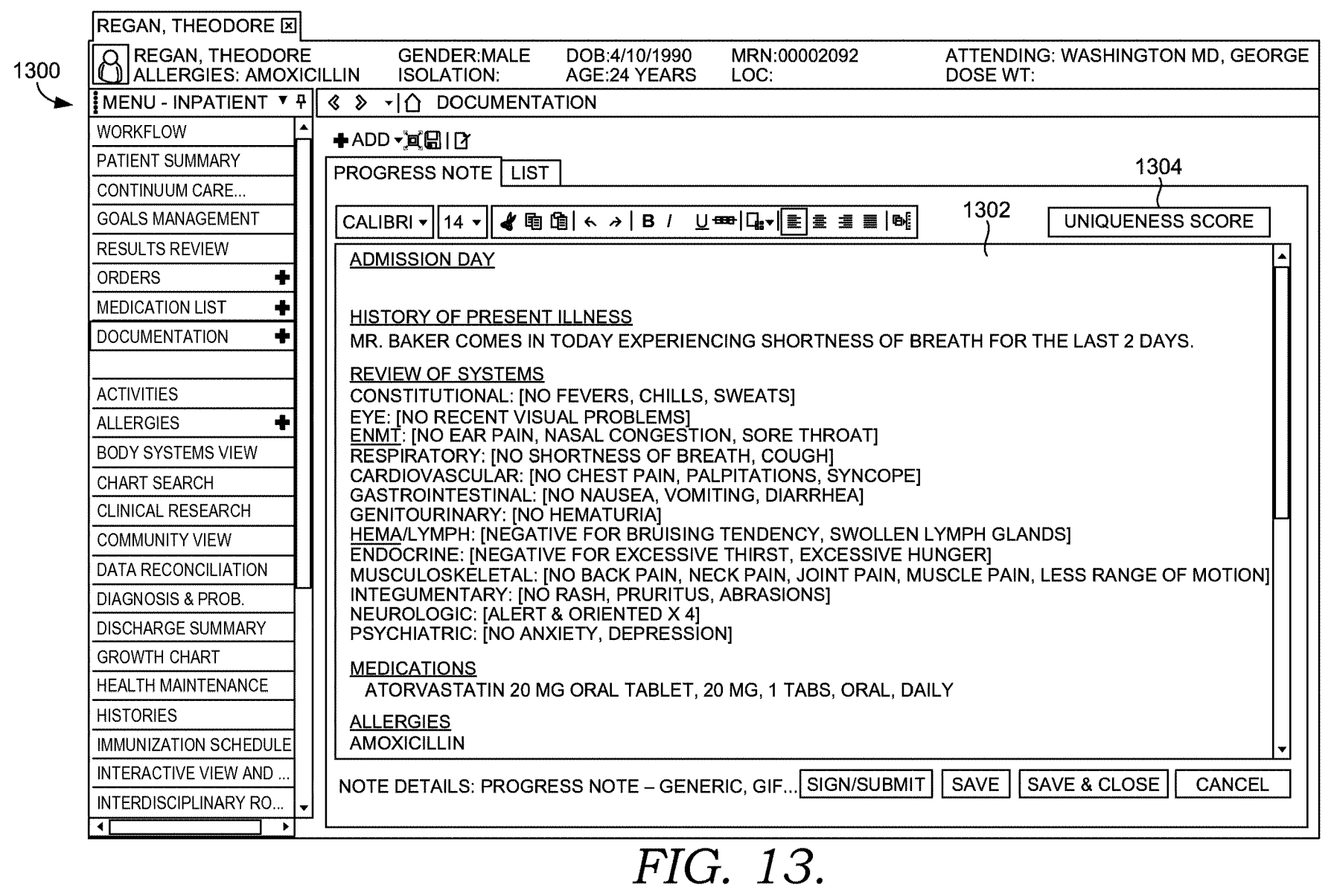

FIG. 13 is an exemplary screenshot 1300 of a user interface displaying a clinical document having an option for a uniqueness score, in accordance with an embodiment herein. The clinical document 1302 displayed in FIG. 13 has been compared to at least one other clinical document, such as a clinical document authored by the same clinician who authored the clinical document 1302, or a clinical document corresponding to the same patient as clinical document 1302. After such comparison, the system may compute a uniqueness score. In the embodiment of FIG. 13, there is a uniqueness score button 1304 that can be selected by a user, such as the author of the clinical document 1302, for the user to be provided with an indication as to how unique the current clinical document is compared to other documents.

As mentioned, in one embodiment, clinical documents that are to be compared may also be for different patients but authored by the same clinician. This could potentially identify clinicians who write the same or similar notes for different patients.

As FIG. 13 illustrates a uniqueness score button 1304, FIG. 14 illustrates an exemplary screenshot 1400 of a user interface displaying a clinical document having a uniqueness score. The clinical document 1402 in FIG. 14 has been or is currently being created by a user. The uniqueness score button 1404 has been selected by the user, and as such, a uniqueness score 1406 is displayed on the user interface. Here, the uniqueness score is 15, which is relatively low. This score indicates to the user that only a small portion of the clinical document 1402 has been found to be the same or similar to other clinical documents, and that much of the text has been copied from one or more other clinical documents, and that the current clinical document is not particularly unique. The uniqueness score may be computed similarly to how the risk level is computed, described herein in relation to FIG. 6. For instance, the computation of the score may take into account one or more factors, such as a straight comparison of text, temporal patterns in the text that are repeated in different clinical documents, phrases that are statistically improbable to be repeated on different days, repeated spelling errors, large portions of text that are repeated, and the like. In addition or alternative to a numerical score, the severity of the score could be indicated to the user by way of a series of colors, for example. For instance, green could indicate "no problems," yellow could indicate "possible problems," and red could indicate "likely problems." Other ways of providing this indication to the user are contemplated to be within the scope of embodiments herein.

Referring to FIG. 15, an exemplary screenshot 1500 is shown of a user interface displaying an indication of statistically improbable similarities in two clinical documents, in accordance with an embodiment herein. The clinical document displayed on the user interface of FIG. 15 includes a sentence that is underlined, referred to as item 1502, and a word that has a box around it, referred to as item 1504. The type of indication used, including highlighting, underlining, using different colors, etc., can be varied, as long as the indication sets apart that sentence, phrase, or word from the rest of the document. The underlined sentence (item 1502) is underlined to bring it to the attention of the user, as it could be determined that a cardiology consult being ordered on two different days or two different points in time may be unlikely. The unlikeliness of this event could be determined on a case-by-case basis. For instance, if the patient is being seen for a heart condition, this may be a likely scenario. However, if the patient is being seen for another condition unrelated to the heart, it would be rare and unlikely that a cardiology consult would be ordered on two different days. The word "tonight" is brought to the user's attention for being a temporal word. It has been determined here that it would be statistically unlikely for not only two cardio consults to be ordered on two different days for the particular patient, but also for both consults to be ordered for "tonight." As mentioned, other ways of bringing suspect sentences, phrases, words, etc., to the user's attention are contemplated to be within the scope of embodiments herein.

The embodiment described above with respect to FIG. 15 may be utilized as a user is inputting data into a clinical document. This may be done to engage the user and bring to their attention portions of the clinical document that may have been inappropriately copied. The time-sensitive term, "tonight," may have been found in two consecutive notes. While this embodiment utilizes a time-sensitive term, other indications of potential cloning could also be brought to the user's attention.

Figure 16:
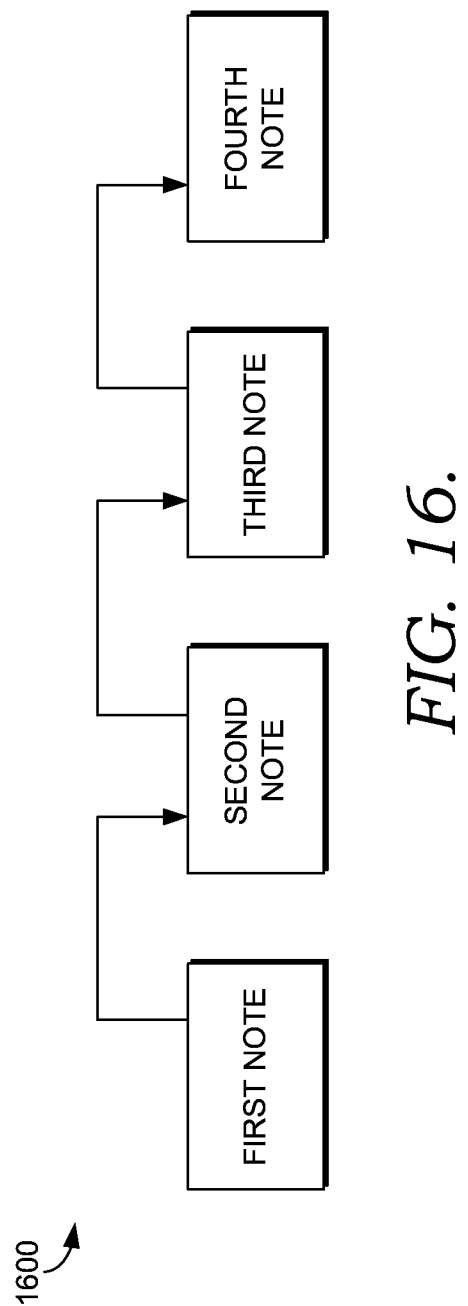
FIG. 16 is a diagram of a comparison of clinical documents that were created on different days, in accordance with an embodiment herein.

FIG. 16 is a diagram 1600 of a comparison of clinical documents that were created at different times, in accordance with an embodiment herein. In embodiments described herein, a clinician may utilize a comparison of various documents to catch up on the care of a patient. As shown here, if the clinician has not seen the patient in several days, or is seeing and caring for the patient for the first time, it would be beneficial to read previous documents corresponding to that patient. However, simply reading each of the notes is time consuming and makes it difficult for the clinician to know exactly what has changed in relation to the patient since the patient was first admitted to a hospital or otherwise first seen by a clinician. For example, using the embodiment of FIG. 16, if the clinician is seeing the patient on day 5 of the patient's care, it may be beneficial for the clinician to compare clinical documents from a first point in time to a second point in time (e.g., day 1 to day 2, first time to second time in the same day), then from the second point in time to a third point in time, then from the third point in time to a fourth point in time, and so on. This gives the clinician an accurate picture of how the patient has or has not progressed since day 1.

Turning to FIG. 17, an exemplary screenshot 1700 of a user interface is depicted displaying an indication of differences between two clinical documents, in accordance with an embodiment herein. A first clinical document 1702 is being compared to a second clinical document 1704. The differences between the two documents are being displayed for the user. Items 1706 and 1708 indicate text in the first clinical document 1702 that is not present in the second clinical document 1704, and items 1710 and 1712 indicate text from the second clinical document 1704 that is not present in the first clinical document 1702. Additionally, to assist the clinician to quickly compare different sequential documents, a backward iteration button 1714 and a forward iteration button 1716 are provided. The clinician can then quickly iterate through sequential clinical documents to catch up on the patient's care.

FIG. 18 is a flow diagram of a method 1800 of detecting similarities in identified passages of clinical documents, in accordance with an embodiment herein. Initially, at block 1802, an identification of a first clinical document and a second clinical document that are to be compared to detect similarities is received. The first and second clinical documents may be associated with a same patient or may be authored by the same clinician. At block 1804, a first section of the first clinical document is determined so that it can be compared to a comparable section of the second clinical document. In an aspect, the first section is determined based on the first section having content that is expected to change from a first point in time corresponding to the first clinical document being completed to a subsequent point in time corresponding to the second clinical document being completed. At block 1806, the first section of the first clinical document is compared to the comparable section of the second clinical document. As shown at block 1808, a first set of passages is identified in the comparable section of the second clinical document, the first set of passages being repeated in a second set of passages in the first section of the first clinical document. At block 1810, it is determined that at least a portion of the passages in the first set of passages is statistically unlikely to be repeated from the second set of passages, and at block 1812, a report is automatically generated. As used herein, the first clinical document may be the most recent clinical document completed for the patient, the most recent clinical document authored by the same clinician who authored the second clinical document, the most recent clinical document that is the same type as the second clinical document, or the most similar clinical document to the second clinical document.

The report may be generated utilizing the first and second sets of passages. In one embodiment, the report is generated automatically and without any human intervention. The report may indicate, at least, the similarities between the first set of passages and the second set of passages. The report could also include a ranking or a score for the first clinical document that has been compared to the second clinical document. The ranking could be computed for just the first section of the first clinical document, or for the entire first clinical document as a whole. The ranking may indicate a relative risk of the second clinical document having the first set of passages in the comparable section that is repeated in the second set of passages in the first section of the first clinical document, or may indicate a relative risk of the first clinical document having the second set of passages in the first section that is repeated in the first set of passages in the comparable section of the second clinical document. In embodiments, the ranking may be based on at least one of a text similarity measurement, a quantity of identical phrases or sentences having temporal patterns, a quantity of identical phrases or sentences that are statistically improbable to be repeated, a quantity of identical phrases or sentences having charge-related patterns, or a quantity of phrases or sentences describing clinical procedures or occurrences that are unlikely to repeat from the first point in time corresponding to the first clinical document to the second point in time corresponding to the second clinical document. As used herein, temporal patterns are sequences of words that reference a particular day, a week, a time of day, etc. Charge-related patterns reference details of the clinician's visit with the patient, such as procedures performed. The text similarity measurement may be a simple analysis of a comparison between words in the documents.

FIG. 19 is a flow diagram of a method 1900 of detecting similarities in identified passages of clinical documents, in accordance with an embodiment herein. Initially, at block 1902, text of a second clinical document that is the same or similar to text of a first clinical document is identified. The first and second clinical documents may be associated with the same patient or may be authored by the same clinician. The first and/or second clinical documents may be progress notes, discharge summaries, etc. Text of the first clinical document that is statistically unlikely to be repeated in the text of the second clinical document may be determined. In one aspect, a user may submit a selection, such as on a user interface, of the first and second clinical documents that are to be compared. The first and second clinical documents may then be retrieved from an electronic storage database, such as an electronic medical record (EMR) associated with the patient. At block 1904, a ranking is computed for the second clinical document in relation to the first clinical document. The ranking indicates a relative risk of the second clinical document having text that is the same or similar to the text of the first clinical document. As mentioned, in addition or alternative to a numerical score, the severity of the score could be indicated to the user by way of a series of colors, for example. For instance, green could indicate "no problems," yellow could indicate "possible problems," and red could indicate "definite problems." Other ways of providing this indication to the user are contemplated to be within the scope of embodiments herein. For example, areas having uninteresting or non-problematic similarities may be collapsed or other visual techniques for emphasizing particular areas (bolding, marking to the side of similar passages, etc.) may be used. At block 1906, transform portions of the first and second clinical documents based on the same or similar or similar data. At block 1908, a report is generated that includes the computed ranking and data that has been transformed from the text of the first and second clinical documents to indicate the similarities between the two documents. In alternative embodiments, the differences between the documents may be indicated instead of the similarities. In one aspect, the report may be used to audit clinical documents at a particular healthcare facility to ensure the clinical documents are in compliance.

Turning now to FIG. 20, a flow diagram is shown of a method 2000 of detecting similarities between clinical documents, in accordance with an embodiment herein. It is noted that in the method 2000 of claim 20, the clinician or other user may be currently writing a progress note or some other note for the patient. These methods may be used to engage the clinician as he or she is writing the note, which could prevent unauthorized or inappropriate copying of previous notes. While the user may be entering text into the document by way of a keyboard or some other input device, the user could also input data by way of a dictation device or some other method. All forms of data input are contemplated to be included in embodiments provided herein.

Initially, at block 2002, it is detected that a clinician is currently inputting data into a first clinical document that is associated with a patient. At block 2004, a selectable option is provided on a user interface into which the clinician is currently inputting data. If selected, the selectable option provides an indication of similarities between the first clinical document and a second clinical document. At block 2006, an indication is received that the selectable option has been selected by the clinician. At block 2008, an algorithm is applied to identify the second clinical document from a plurality of clinical documents. The second clinical document may be identified so that it can be compared to the first clinical document. The algorithm may take into account one or more times associated with the first clinical document and the second clinical document, an identity of the clinician who authored the first and second clinical documents, an identity of the patient associated with the first and second clinical documents, a type of the first clinical document, contents of the first clinical document, etc. A type of document could include whether the document is a discharge note, a progress note, a physical therapy note, a department or category associated with the patient visit (e.g., NICU, cardiology, neurology), etc. At block 2010, data in the first clinical document and the second clinical document is transformed to generate a new representation of the first clinical document that indicates similarities between the first and second clinical documents. In one aspect, the new representation of the first clinical document is editable. Differences or similarities may be indicated by any means, including underlining, highlighting, use of colors, etc. The term new representation is not meant to be limiting in any respect. For instance, a new representation of a document, in one instance, is a new document, while in other instances, is a marked up display version or a new rendering of the document.

Referring to FIG. 21, a flow diagram is shown of a method 2100 of detecting similarities between clinical documents, in accordance with an embodiment herein. At block 2102, an indication is received that a clinician is currently inputting data into a first clinical document by way of a user interface of a computing device. At block 2104, a second clinical document that is to be compared to a first clinical document is algorithmically identified so that similarities can be identified. The second clinical document may have been created prior to the creation of the first clinical document. The algorithmic identification may be based on, for example, one or more of times associated with the first clinical document and the second clinical document, an identity of the clinician who authored the first and second clinical documents, an identity of the patient associated with the first and second clinical documents, a type of the first clinical document, contents of the first clinical document, etc. At block 2106, while the clinician is inputting data into the first clinical document, indications of similarities between at least a portion of the data of the first clinical document and at least a portion of data of the second clinical document are displayed. In one aspect, both clinical documents are displayed on the user interface at the same time. Further, the clinician may be able to edit the first clinical document while the indications of the similarities between the documents are displayed.

In one instance, an indication of a hover action by the user over one of the indications of the similarities is received. In response to the hover action, a detailed explanation of a problem associated with the similarity between the data of the first clinical document and the data of the second clinical document is provided.

Figure 22:
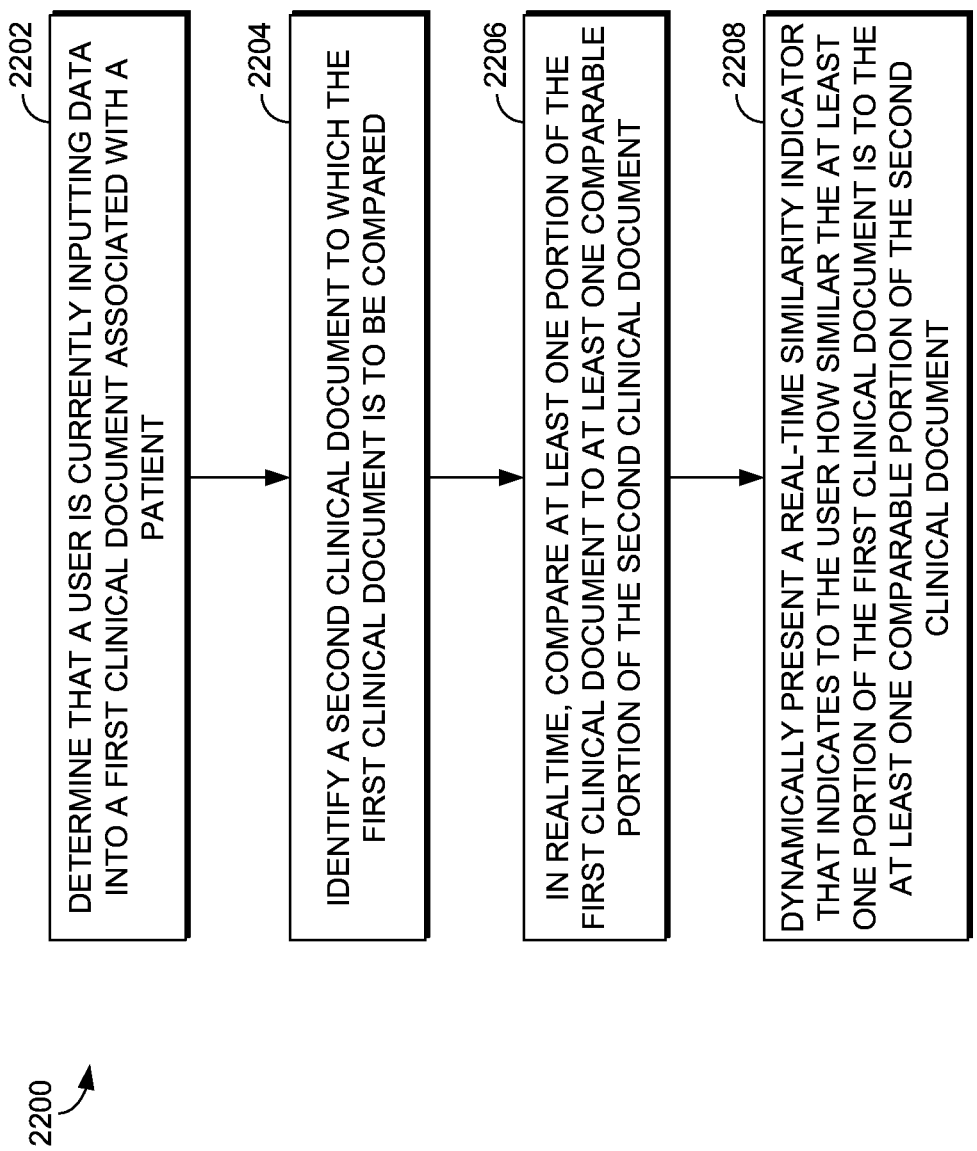

Turning to FIG. 22, a flow diagram is shown of a method 2200 of detecting similarities between clinical documents, in accordance with an embodiment herein. At block 2202, it is determined that a user is currently inputting data into a first clinical document associated with a patient. At block 2204, a second clinical document is identified that is to be compared to the first clinical document. At block 2206, in real time, at least one portion of the first clinical document is compared to a comparable portion of the second clinical document. At block 2208, a real-time similarity indicator is dynamically presented that indicates to the user how similar the portion of the first clinical document is to the comparable portion of the second clinical document. In one aspect, the real-time similarity indicator is a score that is dynamically computed at predetermined intervals of time. The real-time similarity indicator may change color based on whether a similarity of the first clinical document when compared to the second clinical document exceeds a predetermined threshold.

In an embodiment, the score is determined based on at least one of a text similarity measurement, a quantity of identical phrases or sentences having temporal patterns, a quantity of identical phrases or sentences that are statistically improbable to be repeated, a quantity of identical phrases or sentences having charge-related patterns, or a quantity of phrases or sentences describing clinical procedures or occurrences that are unlikely to repeat from the first point in time corresponding to the first clinical document to the second point in time corresponding to the second clinical document. As used herein, temporal patterns are sequences of words that reference a particular day, a week, a time of day, any other point in time, etc. Charge-related patterns reference details of the clinician's visit with the patient, such as how the patient is feeling on a particular day or even specific dosages of medication that the patient is currently taking. The text similarity measurement may be a simple analysis of a comparison between words in the documents. Even further, the score may be based on identical phrases or sentences that are repeated that occur infrequently with respect to a corpus of clinical documents, such as those stored in a data store.

Figure 23:
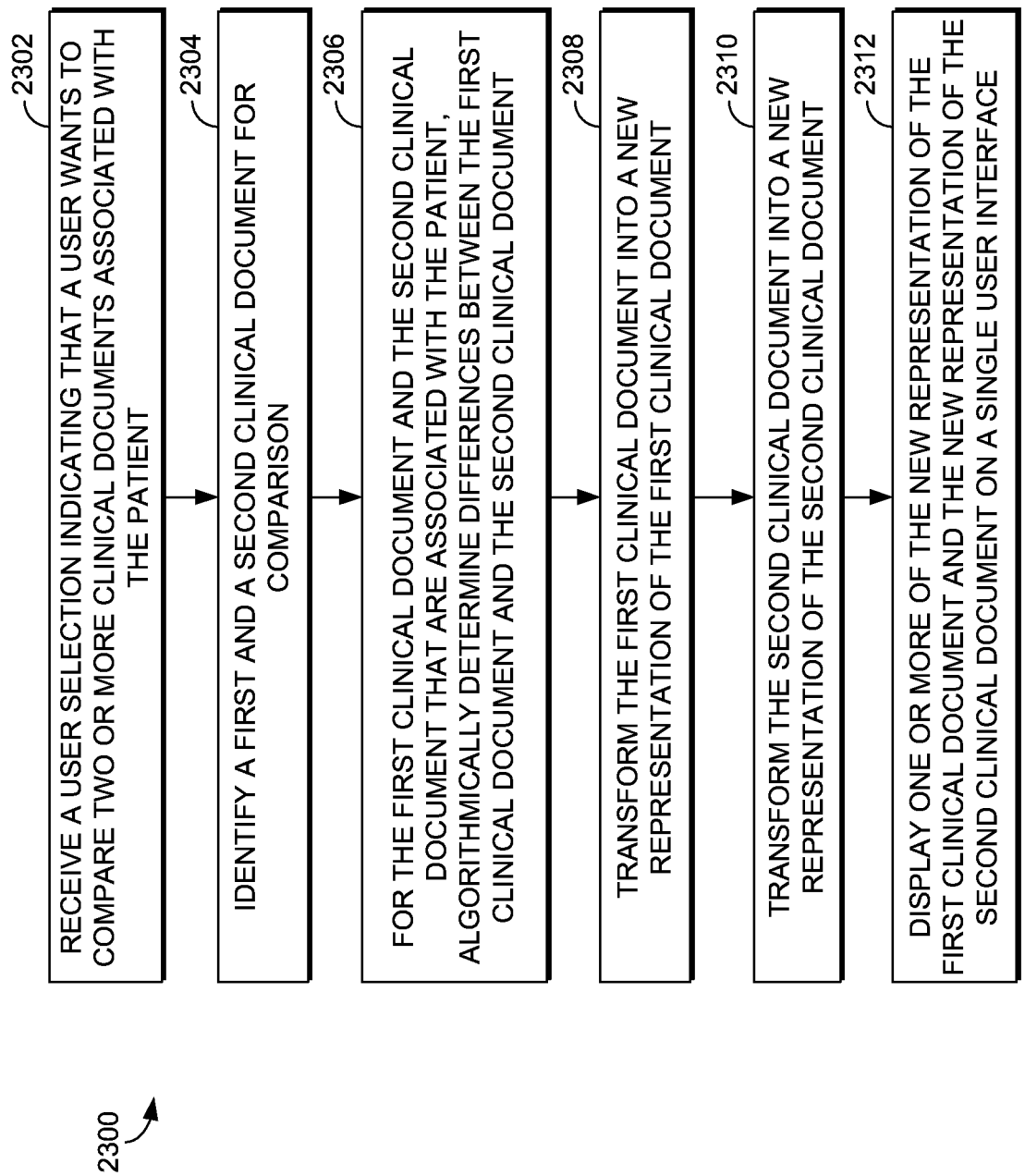
FIGS. 23-25 are flow diagrams of methods of detecting incremental changes in clinical documents associated with a patient, in accordance with embodiments herein.

FIG. 23 is a flow diagram of a method 2300 of detecting incremental changes in clinical documents associated with a patient, in accordance with an embodiment herein. At block 2302, a first clinical document and a second clinical document are identified. For example, for an inpatient daily progress note, the source document, or the second clinical document to which the target document, or the first clinical document is compared, may be the previous day's daily progress note. For a nursing note, the previous shift note could be used. For an outpatient clinic visit, the clinic note from the last visit to the same specialty clinic may be used for comparison. At block 2304, a user selection is received indicating that a user wants to compare two or more clinical documents associated with the patient. This may enable the user to become up-to-date on the patient's care. It may be statistically determined which portions of the first and second clinical documents are to be compared. At block 2306, for a first clinical document and a second clinical document that are associated with the same patient, differences between the first and second clinical documents are algorithmically determined. In one aspect, the first clinical document was created prior to the second clinical document. In some embodiments, only differences from the statistically determined portions of the documents are algorithmically determined. At block 2308, the first clinical document is transformed into a new representation of the first clinical document. The new representation comprises an indication of data in the first clinical document that is not in the second clinical document. Similarly, at block 2310, the second clinical document is transformed into a new representation of the second clinical document. The new representation comprises an indication of data in the second clinical document that is not in the first clinical document. At block 2312, the new representations of the first and second clinical documents are displayed on a single user interface.

In one aspect, changes from the second clinical document to a third clinical document are algorithmically determined, where the second clinical document was created prior to the third clinical document. The second clinical document may be transformed into a second new representation of the second clinical document, where the second new representation of the second clinical document comprises an indication of data in the second clinical document that is not in the third clinical document. Further, the third clinical document may be transformed into a new representation of the third clinical document, where the new representation of the third clinical document comprises an indication of data in the third clinical document that is not in the second clinical document. The second new representation of the second clinical document and the new representation of the third clinical document are displayed on a single user interface.

Figure 24:
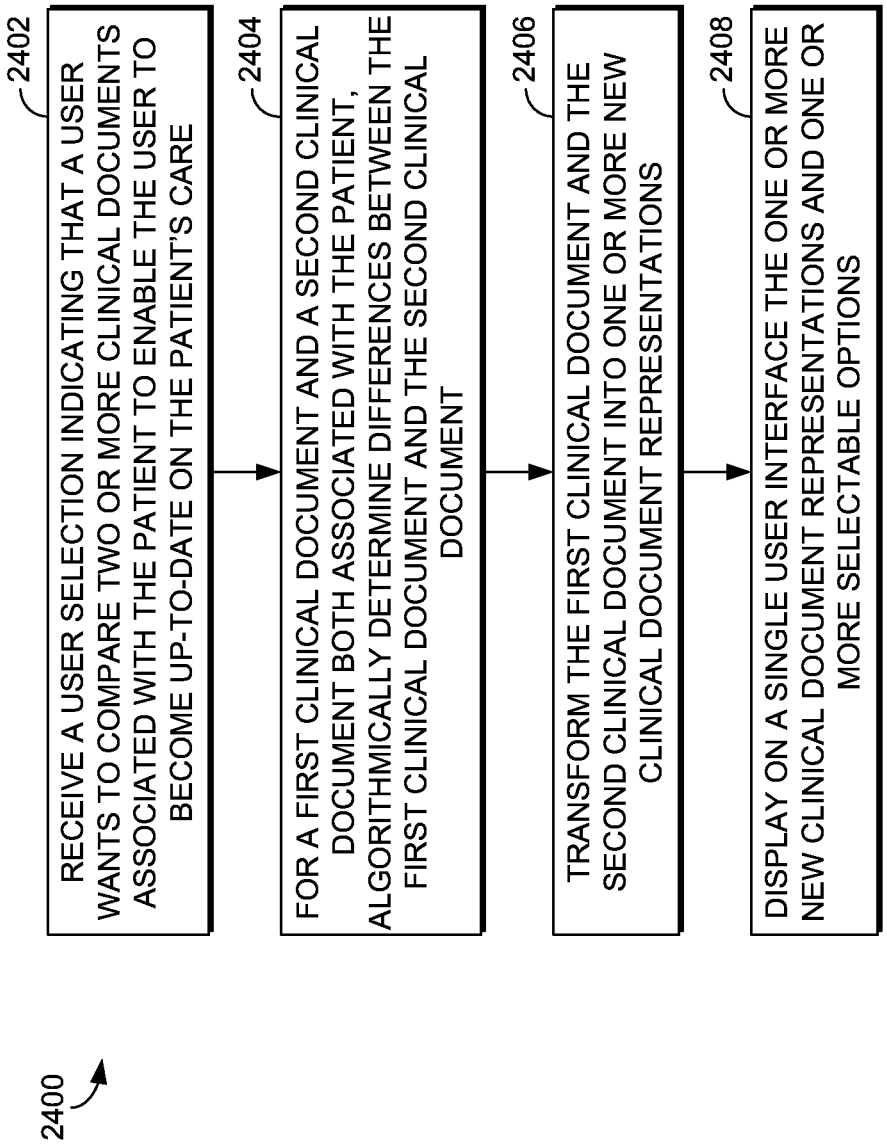

FIG. 24 is a flow diagram of a method 2400 of detecting incremental changes in clinical documents associated with a patient, in accordance with an embodiment herein. At block 2402, a user selection is received indicating that a user wants to compare two or more clinical documents associated with a patient to enable the user to become up-to-date on the patient's care. At block 2404, for a first clinical document and a second clinical document associated with the patient, differences between the first and second clinical documents are algorithmically determined. At block 2406, the first clinical document and the second clinical document are transformed into a new clinical document representation. The new clinical document representation comprises at least an indication of data in the second clinical document that is different than the first clinical document.

At block 2408, the new clinical document representation and one or more selectable options are displayed on a single user interface. The selectable options allow the user to compare the first clinical document or the second clinical document with other clinical documents associated with the patient. In one aspect, the new representations of the first and second clinical documents are displayed on a single user interface. The first clinical document could have been created prior to the second clinical document, or vice versa. Further, the first and second clinical documents could have been created on consecutive days. Even further, the two documents may be created by the same clinician, or by different clinicians. The new clinical document representation may comprise a new representation of the first clinical document and a new representation of the second clinical document, which may be displayed on a single user interface. The new representation may include annotations that help the user to quickly find and understand the differences between the two or more documents.

Figure 25:
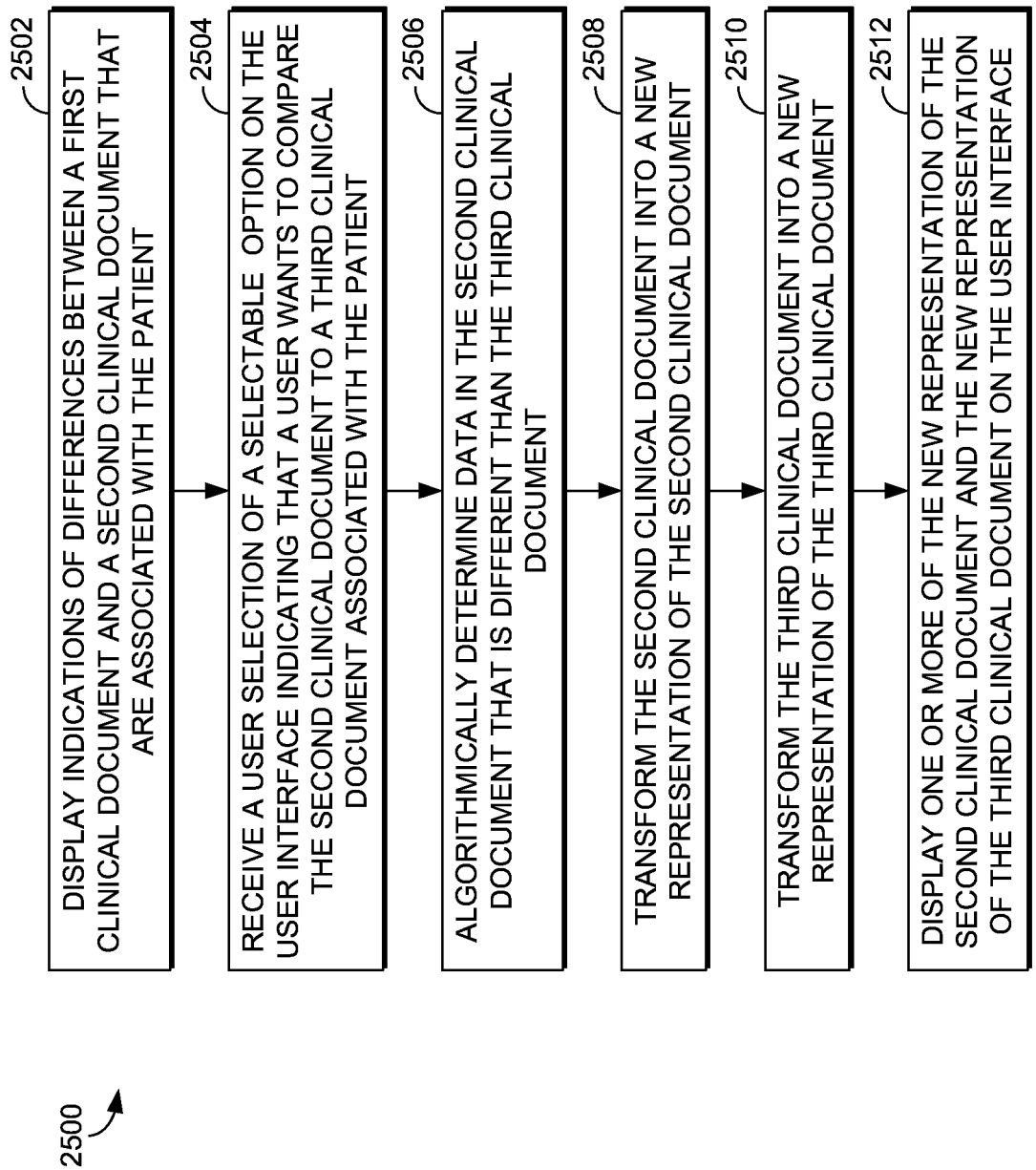

FIG. 25 is a flow diagram of a method 2500 of detecting incremental changes in clinical documents associated with a patient, in accordance with an embodiment herein. At block 2502, indications of differences between a first clinical document and second clinical document associated with a patient are displayed. At block 2504, a user selection of a selectable option on the user interface is received indicating that a user wants to compare the second clinical document to a third clinical document associated with the patient. At block 2506, data in the second clinical document that is different than data in the third clinical document is algorithmically determined. At block 2508, the second clinical document is transformed into a new representation of the second clinical document, while at block 2510 the third clinical document is transformed into a new representation of the third clinical document. The new representations indicate data in those documents that is not in the other document to which it is being compared. At block 2512, the new representations of the second and third clinical documents are displayed on the user interface. The new representations may include annotations that help the user to quickly find and understand the differences between the two or more documents. Here, the second clinical document may have been created prior to the third clinical document, and they may have even been created on consecutive days.

In one embodiment, a user selection may be received indicating that the user wants to compare the third clinical document to a fourth clinical document. Data in the third clinical document that is different than the fourth clinical document is algorithmically determined, in addition to data in the fourth clinical document that is different than the third clinical document. The third clinical document is transformed into a second new representation of the third clinical document, the second new representation of the third clinical document comprising an indication of the data in the third clinical document that is not in the fourth clinical document. The fourth clinical document is transformed into a new representation of the fourth clinical document, the new representation of the fourth clinical document comprising an indication of the data in the fourth clinical document that is not in the third clinical document. Further, the second new representation of the third clinical document and the new representation of the fourth clinical document are displayed on the user interface.

Aspects provided herein been described in relation to particular embodiments, which are intended in all respects to be illustrative rather than restrictive. Further, aspects provided herein are not limited to these embodiments, and variations and modifications may be made without departing from the scope described herein.

What is claimed is:

1. One or more non-transitory computer-readable media having computer-executable instructions embodied thereon that, when executed by a computing device, perform a method of detecting similarities between two or more clinical documents within a single patient's record, the method comprising:
   detecting that a clinician is currently inputting data into a first clinical document presented on a graphical user interface (GUI) at a first point in time, wherein the first clinical document is associated with a patient;
   receiving a selection of a selectable option presented on the GUI to trigger a search for a second clinical document from a plurality of clinical documents also associated with the patient;
   identifying the second clinical document, wherein the second clinical document comprises a service or publishing date that is prior to or equal to the service or publish date of the first clinical document, wherein the second clinical document is identified based on one or more of clinician, patient, or type of document, and wherein the plurality of clinical documents from which the second clinical document is identified is limited based on a status of the clinician being a provider;
   locating a section in the second clinical document that is comparable to a section in the first clinical document based on a character n-gram of a predetermined size that comprises text in the second clinical document that is statistically unlikely to repeat from a second point in time associated with the second clinical document to the first point in time associated with the first clinical document, wherein the text that is statistically unlikely to repeat is determined based on a temporal element or a medication present in the text in the second clinical document;
   transforming at least the section in the first clinical document and at least the section in the second clinical document to generate a new representation of the first clinical document that indicates a similar text between the section in the first clinical document and the section in the second clinical document; and generating a report and communicating the report to the clinician via the GUI, wherein the report comprises an indication of the section in the first clinical document that is statistically unlikely to repeat.

2. The one or more non-transitory computer-readable media of claim 1, wherein the new representation of the first clinical document is editable in real-time.

3. The one or more non-transitory computer-readable media of claim 1, wherein the new representation of the first clinical document also indicates differences between the first clinical document and the second clinical document.

4. The one or more non-transitory computer-readable media of claim 1, wherein the similar text between the first clinical document and the second clinical document are indicated by one of highlighting or underlining.

5. The one or more non-transitory computer-readable media of claim 1, wherein the second clinical document is also authored by the clinician.

6. The one or more non-transitory computer-readable media of claim 1, further including assigning a score to the first clinical document, wherein the score is determined based on one or more of,
- a text similarity measurement,
- a quantity of identical phrases or sentences having temporal patterns,
- a quantity of identical phrases or sentences that are statistically improbable to be repeated,
- a quantity of identical phrases or sentences having charge-related patterns, and 'a quantity of phrases or sentences describing clinical procedures or occurrences that are unlikely to be repeated from the second point in time associated with the second clinical document to the first point in time associated with the first clinical document.

7. One or more non-transitory computer-readable media having computer-executable instructions embodied thereon that, when executed by a computing device, perform a method of comparing two or more clinical documents within a single patient's record, the method comprising:
- receiving an indication that a user is currently inputting data into a first clinical document associated with a patient that is presented on a graphical user interface (GUI);
- determining a subset of clinical documents from a plurality of clinical documents also associated with the patient, based on whether the user is a clinician or a patient, wherein the subset of clinical documents comprise a service or publishing date that is prior to or equal to the service or publish date of the first clinical document;
- from the subset of clinical documents, identifying a section in a second clinical document that is comparable to a section in the first clinical document based on a character n-gram of a predetermined size, wherein the section in the first clinical document comprises one or more words or phrases that are statistically unlikely to repeat from a second point in time associated with the second clinical document to a first point in time associated with the first clinical document, wherein the one or more words or phrases that are statistically unlikely to repeat are determined based on a temporal element or a medication present in the one or more words or phrases; and
- while the user is inputting the data into the first clinical document, displaying a comparison between the section of the second clinical document that is comparable to the section of the first clinical document, the comparison indicating to the user the one or more words or phrases that are statistically unlikely to repeat in the first clinical document.

8. The one or more non-transitory computer-readable media of claim 7, wherein the first clinical document and the second clinical document are simultaneously displayed on the GUI.

9. The one or more non-transitory computer-readable media of claim 7, wherein the user can edit the first clinical document while the comparison between the section of the second clinical document that is comparable to the section of the first clinical document is displayed on the GUI.

10. The one or more non-transitory computer-readable media of claim 7, further comprising receiving an indication of a hover action over the comparison.

11. The one or more non-transitory computer-readable media of claim 10, further comprising in response to the hover action, presenting on the GUI, an explanation of a problem associated with the comparison between the section of the second clinical document that is comparable to the section of the first clinical document.

12. A system for detecting similarities between two or more clinical documents associated with a single patient, the system comprising:
- one or more processors; and
- one or more non-transitory computer storage media storing computer- useable instructions that, when used by the one or more processors, cause the one or more processors to:
- determine that a user is currently inputting data into a first clinical document presented on a graphical user interface (GUI) associated with a patient;
- from at least one database storing a plurality of clinical documents, identify a section of a second clinical document also associated with the patient that is comparable to a section of the first clinical document based on a character n-gram of a predetermined size that comprises text in the second clinical document that is statistically unlikely to repeat from a second point in time associated with the second clinical document to the first point in time associated with the first clinical document, wherein the text that is statistically unlikely to repeat is determined based on a temporal element or a medication present in the text in the section of the second clinical document;
- compare the section of the first clinical document to the section of the second clinical document that is comparable to the section of the first clinical document; and
- present in the GUI, a real-time similarity indicator that indicates to the user how similar the section of the first clinical document is to the section of the second clinical document.

13. The system of claim 12, wherein the real-time similarity indicator is a score.

14. The system of claim 13, further comprising determining the score represented by the real-time similarity indicator at predetermined intervals of time.

15. The system of claim 13, wherein the real-time similarity indicator is determined based on one or more of,
- a text similarity measurement,
- a quantity of identical phrases or sentences having temporal patterns,
- a quantity of identical phrases or sentences that are statistically improbable to be repeated, a quantity of identical phrases or sentences having charge-related patterns, and a quantity of phrases or sentences describing clinical procedures or occurrences that are unlikely to repeat from a second point in time corresponding to the second clinical document to a first point in time corresponding to the first clinical document.

16. The system of claim 15, wherein the temporal patterns reference a particular day or a time of day.

17. The system of claim 15, wherein the charge-related patterns reference details of the clinician's visit with the patient.

18. The system of claim 15, wherein the score is further based on identical phrases or sentences that are repeated that occur infrequently with respect to a corpus of clinical documents.

19. The system of claim 12, wherein the real-time similarity indicator changes color based on whether a similarity of the first clinical document when compared to the second clinical document exceeds a predetermined threshold.

* * * * *